(12) United States Patent
Schlesinger et al.

(10) Patent No.: US 10,806,803 B2
(45) Date of Patent: Oct. 20, 2020

(54) COMPOSITIONS FOR TARGETING MACROPHAGES AND OTHER CD206 HIGH EXPRESSING CELLS AND METHODS OF TREATING AND DIAGNOSIS

(71) Applicants: OHIO STATE INNOVATION FOUNDATION, Columbus, OH (US); CARDINAL HEALTH 414, LLC, Dublin, OH (US); Frederick O. Cope, Dublin, OH (US)

(72) Inventors: Larry Schlesinger, Powell, OH (US); Eric Bachelder, Dublin, OH (US); Frederick O. Cope, Dublin, OH (US)

(73) Assignees: OHIO STATE INNOVATION FOUNDATION, Columbus, OH (US); CARDINAL HEALTH 414, LLC, Dublin, OH (US)

( * ) Notice: Subject to any disclaimer, the term of this patent is extended or adjusted under 35 U.S.C. 154(b) by 0 days.

(21) Appl. No.: 15/326,985

(22) PCT Filed: Jul. 17, 2015

(86) PCT No.: PCT/US2015/041019
§ 371 (c)(1),
(2) Date: Jan. 17, 2017

(87) PCT Pub. No.: WO2016/011419
PCT Pub. Date: Jan. 21, 2016

(65) Prior Publication Data
US 2017/0209584 A1 Jul. 27, 2017

Related U.S. Application Data

(60) Provisional application No. 62/027,733, filed on Jul. 22, 2014, provisional application No. 62/027,220, filed on Jul. 21, 2014, provisional application No. 62/027,193, filed on Jul. 21, 2014, provisional application No. 62/025,991, filed on Jul. 17, 2014.

(51) Int. Cl.
| | |
|---|---|
| *A61K 49/00* | (2006.01) |
| *A61K 47/40* | (2006.01) |
| *A61K 31/44* | (2006.01) |
| *A61K 31/704* | (2006.01) |
| *A61K 31/4409* | (2006.01) |
| *A61K 47/61* | (2017.01) |
| *C08B 37/02* | (2006.01) |

(52) U.S. Cl.
CPC ...... *A61K 49/0032* (2013.01); *A61K 31/4409* (2013.01); *A61K 31/704* (2013.01); *A61K 47/61* (2017.08); *A61K 49/0054* (2013.01); *C08B 37/0021* (2013.01)

(58) Field of Classification Search
CPC ..... A61K 49/00; A61K 47/40; A61K 31/4409
See application file for complete search history.

(56) References Cited

U.S. PATENT DOCUMENTS

| | | | |
|---|---|---|---|
| 6,036,963 | A | 3/2000 | Weinkauf et al. |
| 6,409,990 | B1 * | 6/2002 | Vera ..................... A61K 49/085 424/9.1 |
| 7,666,979 | B2 | 2/2010 | Fan et al. |
| 2004/0116348 | A1 | 6/2004 | Chau et al. |
| 2004/0122382 | A1 | 6/2004 | Johnson et al. |
| 2005/0042248 | A1 | 2/2005 | Ahmad et al. |
| 2005/0214859 | A1 | 9/2005 | Dransfield et al. |
| 2009/0004218 | A1 | 1/2009 | Hacohen et al. |
| 2009/0311182 | A1 | 12/2009 | Wang et al. |
| 2010/0261875 | A1 | 10/2010 | Dransfield et al. |
| 2013/0330274 | A1 | 12/2013 | Berr et al. |
| 2014/0127301 | A1 | 5/2014 | Alexis et al. |
| 2014/0235790 | A1 | 8/2014 | Stayton et al. |
| 2015/0023876 | A1 | 1/2015 | Cope et al. |

FOREIGN PATENT DOCUMENTS

| | | |
|---|---|---|
| CA | 2484275 C | 3/2011 |
| GB | 1069820 A | 5/1967 |
| JP | 2012516328 A | 7/2012 |
| WO | WO1996/008263 | 3/1996 |
| WO | 2004037305 A1 | 5/2004 |
| WO | 2012/169973 A1 | 12/2012 |
| WO | 2015/013341 | 1/2015 |
| WO | WO2016/011415 | 1/2016 |
| WO | WO2016/011419 | 1/2016 |

OTHER PUBLICATIONS

Xiaojuan Wang et al. A novel delivery system of doxorubicin with high load and pH-responsive release from the nanoparticles of poly (alpha, beta-aspartic acid) derivative, European J Pharm. Sci, 47, 256-264. (Year: 2012).*
Coessens et al., "Synthesis of polyglutamine and dextran conjugates of streptomycin with an acid-sensitive drug-carrier linkage," Journal of Controlled Release, 1996, ol. 38, No. 2, pp. 141-150.
Hongjing et al., "Facile preparation and drug delivery behaviour of novel dextran-based nanogels conjugated with doxorubicin via a pH- labile bond," Journal of Controlled Release, 2013, vol. 172, No. 1, e67-e68.
European Patent Office Extended Search Report for Application No. 15822654.8 dated Mar. 1, 2018 (12 pages).
Allavena, P., M. Chieppa, G. Bianchi, G. Solinas, M. Fabbri, G. Laskarin, and A. Mantovani. 2010. Engagement of the mannose receptor by tumoral mucins activates an immune suppressive phenotype in human tumor-associated macrophages. Clin. Dev. Immunol. 2010: 547179.
Azad, A. K., M. V. Rajaram, and L. S. Schlesinger. 2014. Exploitation of the Macrophage Mannose Receptor (CD206) in Infectious Disease Diagnostics and Therapeutics. J. Cytol. Mol. Biol. 1.
Balkwill, F., and A. Mantovani. 2001. Inflammation and cancer: back to Virchow? Lancet 357: 539-545.

(Continued)

*Primary Examiner* — Michael G. Hartley
*Assistant Examiner* — Jagadishwar R Samala
(74) *Attorney, Agent, or Firm* — Michael Best & Friedrich LLP

(57) ABSTRACT

Provided are compounds and compositions for targeting macrophages and other CD206 high expressing cells.

11 Claims, 8 Drawing Sheets

(56) References Cited

OTHER PUBLICATIONS

Banerji, S., J. Ni, S. X. Wang, S. Clasper, J. Su, R. Tammi, M. Jones, and D. G. Jackson. 1999. LYVE-1, a new homologue of the CD44 glycoprotein, is a lymph-specific receptor for hyaluronan. J Cell Biol. 144: 789-801.
Beasley, N. J., R. Prevo, S. Banerji, R. D. Leek, J. Moore, T. P. van, G. Cox, A. L. Harris, and D. G. Jackson. 2002. Intratumoral lymphangiogenesis and lymph node metastasis in head and neck cancer. Cancer Res. 62: 1315-1320.
Choe and Lee, "Targeted in Vivo Imaging of Angiogenesis: Present Status and Perspectives," 2007, Current Pharmaceutical Design, 13:17-31.
Choi, Y. K., B. A. Fallert Junecko, C. R. Klamar, and T. A. Reinhart. 2013. Characterization of cells expressing lymphatic marker LYVE-1 in macaque large intestine during simian immunodeficiency virus infection identifies a large population of nonvascular LYVE-1(+)/DC-SIGN(+) cells. Lymphat. Res. Biol. 11: 26-34.
Coughlin, A., and V. A. Resto. 2010. Oral cavity squamous cell carcinoma and the clinically n0 neck: the past, present, and future of sentinel lymph node biopsy. Curr. Oncol. Rep. 12: 129-135.
Dave, S. S., K. Fu, G. W. Wright, L. T. Lam, P. Kluin, E. J. Boerma, T. C. Greiner, D. D. Weisenburger, A. Rosenwald, G. Ott, H. K. Muller-Hermelink, R. D. Gascoyne, J. Delabie, L. M. Rimsza, R. M. Braziel, T. M. Grogan, E. Campo, E. S. Jaffe, B. J. Dave, W. Sanger, M. Bast, J. M. Vose, J. O. Armitage, J. M. Connors, E. B. Smeland, S. Kvaloy, H. Nolte, R. I. Fisher, T. P. Miller, E. Montserrat, W. H. Wilson, M. Bahl, H. Zhao, L. Yang, J. Powell, R. Simon, W. C. Chan, and L. M. Staudt. 2006. Molecular diagnosis of Burkitt's lymphoma. N. Engl. J. Med. 354: 2431-2442.
Dijkgraaf et al., "Molecular imaging of angiogenesis with SPECT," 2010, Eur. J. Nucl. Med. Mol. Imaging, published online Sep. 21, 2010.
Ellner, S. J., C. K. Hoh, D. R. Vera, D. D. Darrah, G. Schulteis, and A. M. Wallace. 2003. Dose-dependent biodistribution of [(99m)Tc]DTPA-mannosyl-dextran for breast cancer sentinel lymph node mapping. Nucl. Med. Biol. 30: 805-810.
Ellner, S. J., J. Mendez, D. R. Vera, C. K. Hoh, W. L. Ashburn, and A. M. Wallace. 2004. Sentinel lymph node mapping of the colon and stomach using lymphoseek in a pig model. Ann. Surg. Oncol. 11: 674-681.
Engering, A., T. B. Geijtenbeek, S. J. Van Vliet, M. Wijers, L. E. van, N. Demaurex, A. Lanzavecchia, J. Fransen, C. G. Figdor, V. Piguet, and K. Y. van. 2002. The dendritic cell-specific adhesion receptor DC-SIGN internalizes antigen for presentation to T cells. J. Immunol. 168: 2118-2126.
Farinha, P., A. Al-Tourah, K. Gill, R. Klasa, J. M. Connors, and R. D. Gascoyne. 2010. The architectural pattern of FOXP3-positive T cells in follicular lymphoma is an independent predictor of survival and histologic transformation. Blood 115: 289-295.
Gazi, U., and L. Martinez-Pomares. 2009. Influence of the mannose receptor in host immune responses. Immunobiology 214: 554-561.
Geijtenbeek, T. B., S. J. Van Vliet, A. Engering, B. A. 't Hart, and K. Y. van. 2004. Self- and nonself-recognition by C-type lectins on dendritic cells. Annu. Rev. Immunol. 22: 33-54.
Gordon, S. 2002. Pattern recognition receptors: doubling up for the innate immune response. Cell 111: 927-930.
Gordon, S. 2003. Alternative activation of macrophages. Nat. Rev. Immunol. 3: 23-35.
Hattori, Y., S. Kawakami, Y. Lu, K. Nakamura, F. Yamashita, and M. Hashida. 2006. Enhanced DNA vaccine potency by mannosylated lipoplex after intraperitoneal administration. J Gene Med 8: 824-834.
Henning, L. N., A. K. Azad, K. V. Parsa, J. E. Crowther, S. Tridandapani, and L. S. Schlesinger. 2008. Pulmonary surfactant protein a regulates TLR expression and activity in human macrophages. J. Immunol. 180: 7847-7858.

Hoh, C. K., A. M. Wallace, and D. R. Vera. 2003. Preclinical studies of [(99m)Tc]DTPA-mannosyl-dextran. Nucl. Med. Biol. 30: 457-464.
International Search Report and Written Opinion for Application No. PCT/US2015/041009 dated Dec. 29, 2015 (19 pages).
International Search Report and Written Opinion for Application No. PCT/US2015/041019 dated Dec. 4, 2015 (12 pages).
Irjala, H., E. L. Johansson, R. Grenman, K. Alanen, M. Salmi, and S. Jalkanen. 2001. Mannose receptor is a novel ligand for L-selectin and mediates lymphocyte binding to lymphatic endothelium. J. Exp. Med. 194: 1033-1042.
Irjala, H., K. Alanen, R. Grenman, P. Heikkila, H. Joensuu, and S. Jalkanen. 2003. Mannose receptor (MR) and common lymphatic endothelial and vascular endothelial receptor (CLEVER)-1 direct the binding of cancer cells to the lymph vessel endothelium. Cancer Res. 63: 4671-4676.
Jensen, T. O., H. Schmidt, H. J. Moller, M. Hoyer, M. B. Maniecki, P. Sjoegren, I. J. Christensen, and T. Steiniche. 2009. Macrophage markers in serum and tumor have prognostic impact in American Joint Committee on Cancer stage I/II melanoma. J. Clin. Oncol. 27: 3330-3337.
Kamper, P., K. Bendix, S. Hamilton-Dutoit, B. Honore, J. R. Nyengaard, and F. d'Amore. 2011. Tumor-infiltrating macrophages correlate with adverse prognosis and Epstein-Barr virus status in classical Hodgkin's lymphoma. Haematologica 96: 269-276.
Kang, B. K., A. K. Azad, J. B. Torrelles, T. M. Kaufman, A. A. Beharka, E. Tibesar, L. E. Desjardin, and L. S. Schlesinger. 2005. The human macrophage mannose receptor directs *Mycobacterium tuberculosis* lipoarabinomannan-mediated phagosome biogenesis. J Exp. Med 202: 987-999.
Kawakami, S., A. Sato, M. Nishikawa, F. Yamashita, and M. Hashida. 2000. Mannose receptor-mediated gene transfer into macrophages using novel mannosylated cationic liposomes. Gene Ther. 7: 292-299.
Kurahara, H., H. Shinchi, Y. Mataki, K. Maemura, H. Noma, F. Kubo, M. Sakoda, S. Ueno, S. Natsugoe, and S. Takao. 2011. Significance of M2-polarized tumor-associated macrophage in pancreatic cancer. J. Surg. Res. 167: e211-e219.
Lau, S. K., P. G. Chu, and L. M. Weiss. 2004. CD163: a specific marker of macrophages in paraffin-embedded tissue samples. Am. J. Clin. Pathol. 122: 794-801.
Law, S. K. A., K. J. Micklem, J. M. Shaw, X.-P. Zhang, Y. Dong, A. C. Willis, and D. Y. Mason. 1993. A new macrophage differentiation antigen which is a member of the scavenger receptor superfamily. Eur. J. Immunol. 23: 2320-2325.
Lee, C. H., I. Espinosa, S. Vrijaldenhoven, S. Subramanian, K. D. Montgomery, S. Zhu, R. J. Marinelli, J. L. Peterse, N. Poulin, T. O. Nielsen, R. B. West, C. B. Gilks, and M. van de Rijn. 2008. Prognostic significance of macrophage infiltration in leiomyosarcomas. Clin. Cancer Res. 14: 1423-1430.
Lee, S. J., S. Evers, D. Roeder, A. F. Parlow, J. Risteli, L. Risteli, Y. C. Lee, T. Feizi, H. Langen, and M. C. Nussenzweig. 2002. Mannose receptor-mediated regulation of serum glycoprotein homeostasis. Science 295: 1901.
Leek, R. D., C. E. Lewis, R. Whitehouse, M. Greenall, J. Clarke, and A. L. Harris. 1996. Association of macrophage infiltration with angiogenesis and prognosis in invasive breast carcinoma. Cancer Res. 56: 4625-4629.
Leong, S. P., J. Kim, M. Ross, M. Faries, C. R. Scoggins, W. L. Metz, F. O. Cope, and R. C. Orahood. 2011. A phase 2 study of (99m)Tc-tilmanocept in the detection of sentinel lymph nodes in melanoma and breast cancer. Ann. Surg. Oncol. 18: 961-969.
Leon-Rodriguez et al., "The Synthesis and Chelation Chemistry of DOTA—Peptide Conjugates," Bioconjugate chemistry, Jan. 3, 2008, 19(2):391-402.
Li et al., "Cu-Labeled Tetrameric and Octameric RGD Peptides for Small-Animal PET of Tumor avb3 I ntegrin Expression," 2007, J. Nuclear Medicine, 48:1162-1171.
Li et al., "Synthesis and charecterization of a high-affinity $\alpha_v\beta_6$-specific ligand for in vitro and in vivo applications," 2009, Mol. Cancer Ther., 8:5:1239-1249.

(56) References Cited

OTHER PUBLICATIONS

Locke, L. W., M. W. Mayo, A. D. Yoo, M. B. Williams, and S. S. Berr. 2012. PET imaging of tumor associated macrophages using mannose coated 64Cu liposomes. Biomaterials 33: 7785-7793.
Lu, Y., S. Kawakami, F. Yamashita, and M. Hashida. 2007. Development of an antigen-presenting cell-targeted DNA vaccine against melanoma by mannosylated liposomes. Biomaterials 28: 3255-3262.
Luo, Y., H. Zhou, J. Krueger, C. Kaplan, S. H. Lee, C. Dolman, D. Markowitz, W. Wu, C. Liu, R. A. Reisfeld, and R. Xiang. 2006. Targeting tumor-associated macrophages as a novel strategy against breast cancer. J. Clin. Invest 116: 2132-2141.
Mantovani, A., B. Bottazzi, F. Colotta, S. Sozzani, and L. Ruco. 1992. The origin and function of tumor-associated macrophages. Immunol. Today 13: 265-270.
Mantovani, A., S. Sozzani, M. Locati, P. Allavena, and A. Sica. 2002. Macrophage polarization: tumor-associated macrophages as a paradigm for polarized M2 mononuclear phagocytes. Trends Immunol. 23: 549-555.
Marttila-lchihara, F., R. Turja, M. Miiluniemi, M. Karikoski, M. Maksimow, J. Niemela, L. Martinez-Pomares, M. Salmi, and S. Jalkanen. 2008. Macrophage mannose receptor on lymphatics controls cell trafficking. Blood 112: 64-72.
Mattila, M. M., J. K. Ruohola, T. Karpanen, D. G. Jackson, K. Alitalo, and P. L. Harkonen. 2002. VEGF-C induced lymphangiogenesis is associated with lymph node metastasis in orthotopic MCF-7 tumors. Int. J Cancer 98: 946-951.
Maula, S. M., M. Luukkaa, R. Grenman, D. Jackson, S. Jalkanen, and R. Ristamaki. 2003. Intratumoral lymphatics are essential for the metastatic spread and prognosis in squamous cell carcinomas of the head and neck region. Cancer Res. 63: 1920-1926.
Mendez, J., A. M. Wallace, C. K. Hoh, and D. R. Vera. 2003. Detection of gastric and colonic sentinel nodes through endoscopic administration of 99mTc-DTPA-mannosyl-dextran in pigs. J. Nucl. Med. 44: 1677-1681.
Miller, J. L., B. J. de Wet, L. Martinez-Pomares, C. M. Radcliffe, R. A. Dwek, P. M. Rudd, and S. Gordon. 2008. The mannose receptor mediates dengue virus infection of macrophages. PLoS. Pathog. 4: e17.
Mills, C. D., K. Kincaid, J. M. Alt, M. J. Heilman, and A. M. Hill. 2000. M-1/M-2 macrophages and the Th1/Th2 paradigm. J. Immunol. 164: 6166-6173.
Movahedi, K., S. Schoonooghe, D. Laoui, I. Houbracken, W. Waelput, K. Breckpot, L. Bouwens, T. Lahoutte, B. P. De, G. Raes, N. Devoogdt, and J. A. Van Ginderachter. 2012. Nanobody-based targeting of the macrophage mannose receptor for effective in vivo imaging of tumor-associated macrophages. Cancer Res. 72: 4165-4177.
Nahrendorf et al., "F-4V for PET-CT imaging of VCAM-1 expression in inflammatory atherosclerosis," 2009, JACC Cardiovasc. Imaging, 2:10:1213-1222.
Park, S. M., C. E. Angel, J. D. McIntosh, C. M. Mansell, C. J. Chen, J. Cebon, and P. R. Dunbar. 2014. Mapping the distinctive populations of lymphatic endothelial cells in different zones of human lymph nodes. PLoS. One. 9: e94781.
Petrova, T. V., T. Makinen, T. P. Makela, J. Saarela, I. Virtanen, R. E. Ferrell, D. N. Finegold, D. Kerjaschki, S. Yla-Herttuala, and K. Alitalo. 2002. Lymphatic endothelial reprogramming of vascular endothelial cells by the Prox-1 homeobox transcription factor. EMBO J 21: 4593-4599.
Podgrabinska, S., P. Braun, P. Velasco, B. Kloos, M. S. Pepper, and M. Skobe. 2002. Molecular characterization of lymphatic endothelial cells. Proc. Natl. Acad. Sci. U. S. A 99: 16069-16074.
Puig-Kroger, A., D. Serrano-Gomez, E. Caparros, A. Dominguez-Soto, M. Relloso, M. Colmenares, L. Martinez-Munoz, N. Longo, N. Sanchez-Sanchez, M. Rincon, L. Rivas, P. Sanchez-Mateos, E. Fernandez-Ruiz, and A. L. Corbi. 2004. Regulated expression of the pathogen receptor dendritic cell-specific intercellular adhesion molecule 3 (ICAM-3)-grabbing nonintegrin in THP-1 human leukemic cells, monocytes, and macrophages. J Biol Chem 279: 25680-25688.

Rajaram, M. V., B. Ni, J. D. Morris, M. N. Brooks, T. K. Carlson, B. Bakthavachalu, D. R. Schoenberg, J. B. Torrelles, and L. S. Schlesinger. 2011. *Mycobacterium tuberculosis* lipomannan blocks TNF biosynthesis by regulating macrophage MAPK-activated protein kinase 2 (MK2) and microRNA miR-125b. Proc. Natl. Acad. Sci. U. S. A 108: 17408-17413.
Rajaram, M. V., M. N. Brooks, J. D. Morris, J. B. Torrelles, A. K. Azad, and L. S. Schlesinger. 2010. *Mycobacterium tuberculosis* activates human macrophage peroxisome proliferator-activated receptor gamma linking mannose receptor recognition to regulation of immune responses. J Immunol. 185: 929-942.
Roseeuw et al., "Synthesis, Degradation, and Antimicrobial Properties of Targeted Macromolecular Prodrugs of Norfloxacin," Antimicrobial Agents and Chemotherapy, 2003, vol. 47, No. 11, pp. 3435-3441.
Salem, C. E., C. K. Hoh, A. M. Wallace, and D. R. Vera. 2006. A preclinical study of prostate sentinel lymph node mapping with [99mTC]diethylenetetramine pentaacetic acid-mannosyl-dextran. J. Urol. 175: 744-748.
Salmi, M., M. Karikoski, K. Elima, P. Rantakari, and S. Jalkanen. 2013. CD44 binds to macrophage mannose receptor on lymphatic endothelium and supports lymphocyte migration via afferent lymphatics. Circ. Res. 112: 1577-1582.
Schlesinger, L. S. 1993. Macrophage phagocytosis of virulent but not attenuated strains of *Mycobacterium tuberculosis* is mediated by mannose receptors in addition to complement receptors. J. Immunol. 150: 2920-2930.
Shabo, I., and J. Svanvik. 2011. Expression of macrophage antigens by tumor cells. Adv. Exp. Med. Biol. 714: 141-150.
Shabo, I., O. Stal, H. Olsson, S. Dore, and J. Svanvik. 2008. Breast cancer expression of CD163, a macrophage scavenger receptor, is related to early distant recurrence and reduced patient survival. Int. J. Cancer 123: 780-786.
Shi, S. R., M. E. Key, and K. L. Kalra. 1991. Antigen retrieval in formalin-fixed, paraffin-embedded tissues: an enhancement method for immunohistochemical staining based on microwave oven heating of tissue sections. J. Histochem. Cytochem. 39: 741-748.
Skobe, M., T. Hawighorst, D. G. Jackson, R. Prevo, L. Janes, P. Velasco, L. Riccardi, K. Alitalo, K. Claffey, and M. Detmar. 2001. Induction of tumor lymphangiogenesis by VEGF-C promotes breast cancer metastasis. Nat. Med 7: 192-198.
Sosabowski et al., "Conjugation of DOTA-like chelating agents to peptides and radiolabeling with trivalent metallic isotopes," Nature Protocols 1, 2006, 972-976.
Stahl, P., P. H. Schlesinger, E. Sigardson, J. S. Rodman, and Y. C. Lee. 1980. Receptor-mediated pinocytosis of mannose glycoconjugates by macrophages: characterization and evidence for receptor recycling. Cell 19: 207-215.
Tahara, N., J. Mukherjee, H. J. de Haas, A. D. Petrov, A. Tawakol, N. Haider, A. Tahara, C. C. Constantinescu, J. Zhou, H. H. Boersma, T. Imaizumi, M. Nakano, A. Finn, Z. Fayad, R. Virmani, V. Fuster, L. Bosca, and J. Narula. 2014. 2-deoxy-2-[18F]fluoro-D-mannose positron emission tomography imaging in atherosclerosis. Nat. Med. 20: 215-219.
Taylor, P. R., L. Martinez-Pomares, M. Stacey, H. H. Lin, G. D. Brown, and S. Gordon. 2005. Macrophage receptors and immune recognition. Annu. Rev. Immunol. 23: 901-944.
Taylor, P. R., S. Gordon, and L. Martinez-Pomares. 2005. The mannose receptor: linking homeostasis and immunity through sugar recognition. Trends Immunol. 26: 104-110.
Torrelles, J. B., A. K. Azad, L. N. Henning, T. K. Carlson, Schlesinger, L.S. 2008. Role of C-type lectins in mycobacterial infections. Curr. Drug Targets. 9: 102-112 (Abstract provided).
Trubian et al., New Drug Approvals 2013—Pt. XII—Technetium Tc 99m Tilmanocept (LymphoSeek) [online]. The ChEMBL-og. Aug. 30, 2013 [retreived on Nov. 30, 2015]. Retreived from the Internet: <URL: http://chembl.blogspot.com/2013/08/new-drug-approvals-2013-pt-xii.html>, 4 pages.
Uccini et al., "Kaposi's Sarcoma Cells Express the Macrophage-Associated Antigen Mannose Receptor and Develop in Peripheral Blood Cultures of Kaposi's Sarcoma Patients," AJP Mar. 1997, 150: 929-938.

(56) References Cited

OTHER PUBLICATIONS

Vera, D. R., A. M. Wallace, and C. K. Hoh. 2001. [(99m)Tc]MAG(3)-mannosyl-dextran: a receptor-binding radiopharmaceutical for sentinel node detection. Nucl. Med. Biol. 28: 493-498.

Vera, D. R., A. M. Wallace, C. K. Hoh, and R. F. Mattrey. 2001. A synthetic macromolecule for sentinel node detection: (99m)Tc-DTPA-mannosyl-dextran. J. Nucl. Med. 42: 951-959.

Vera, D. R., E. S. Woodle, and R. C. Stadalnik. 1989. Kinetic sensitivity of a receptor-binding radiopharmaceutical: technetium-99m galactosyl-neoglycoalbumin. J. Nucl. Med. 30: 1519-1530.

Vera, D. R., K. A. Krohn, R. C. Stadalnik, and P. O. Scheibe. 1984. Tc-99m galactosyl-neoglycoalbumin: in vitro characterization of receptor-mediated binding. J. Nucl. Med. 25: 779-787.

Wallace, A. M., C. K. Hoh, D. R. Vera, D. D. Darrah, and G. Schulteis. 2003. Lymphoseek: a molecular radiopharmaceutical for sentinel node detection. Ann. Surg. Oncol. 10: 531-538.

Wallace, A. M., C. K. Hoh, K. K. Limmer, D. D. Darrah, G. Schulteis, and D. R. Vera. 2009. Sentinel lymph node accumulation of Lymphoseek and Tc-99m-sulfur colloid using a "2-day" protocol. Nucl. Med. Biol. 36: 687-692.

Wallace, A. M., C. K. Hoh, S. J. Ellner, D. D. Darrah, G. Schulteis, and D. R. Vera. 2007. Lymphoseek: a molecular imaging agent for melanoma sentinel lymph node mapping. Ann. Surg. Oncol. 14: 913-921.

Wallace, A. M., S. J. Ellner, J. Mendez, C. K. Hoh, C. E. Salem, C. M. Bosch, R. C. Orahood, and D. R. Vera. 2006. Minimally invasive sentinel lymph node mapping of the pig colon with Lymphoseek. Surgery 139: 217-223.

Wang et al., "A novel delivery system of doxorubicin with high load and pH-responsive release from the nanoparticles of poly (alpha, beta-aspartic acid) derivative," European Journal of Pharmaceutical Sciences, 2012, vol. 47, pp. 256-264.

Wild, J., D. Robinson, and B. Winchester. 1983. Isolation of mannose-binding proteins from human and rat liver. Biochem. J. 210: 167-174.

Wileman, T., R. L. Boshans, P. H. Schlesinger, and P. H. Stahl. 1984. Monensin inhibits recycling of macrophage mannose-glycoprotein receptors and ligand delivery to lysosomes. Biochem. J. 220: 665-675.

Wilting, J., M. Papoutsi, B. Christ, K. H. Nicolaides, C. S. von Kaisenberg, J. Borges, G. B. Stark, K. Alitalo, S. I. Tomarev, C. Niemeyer, and J. Rossler. 2002. The transcription factor Prox1 is a marker for lymphatic endothelial cells in normal and diseased human tissues. FASEB J 16: 1271-1273.

Yim et al., "Synthesis of DOTA-Conjugated Multimeric [Tyr3] Octreotide Peptides via a Combination of Cu(I)-Catalyzed "Click" Cycloaddition and Thio Acid/Sulfonyl Azide "Sulfo-Click" Amidation and Their in Vivo Evaluation," 2010, J. Med. Chem., 53:3944-3953.

Yu, S. S., C. M. Lau, W. J. Barham, H. M. Onishko, C. E. Nelson, H. Li, C. A. Smith, F. E. Yull, C. L. Duvall, and T. D. Giorgio. 2013. Macrophage-Specific RNA Interference Targeting via "Click", Mannosylated Polymeric Micelles. Mol. Pharm.

International Search Report and Written Opinion for International Application No. PCT/US15/41036, dated Nov. 23, 2015, 10 pages.

Paul C.B., Tertiary Pharmacology Review, Center for Drug Evaluation and Research, Aug. 10, 2011, 134 pages.

Porcheray F., et al., "Macrophage Activation and Human Immunodeficiency Virus Infection: HIV Replication Direct-Macrophages towards a Pro-Inflammatory Phenotype While Previous Activation Modulates Macrophage Susceptibility to Infection and Viral Production," Virology, 2006, vol. 349 (1), pp. 112-120.

European Patent Office Search Report for Application No. 15821443.7 dated Mar. 9, 2018 (13 pages).

Emerson et al., "A Receptor-targeted Fluorescent Radiopharmaceutical for Multireporter Sentinel Lymph Node Imaging," Radiology, 2012, 265(1):186-193.

Jarjour et al., "Fluorescent CD206-targeted Manocept-Cy3 (Mano-Cy3) specifically localizes on macrophages (MPs) derived from rheumatoid arthritis (RA) patients' synovial fluid & is quantitatively greater than that from non-RA patients," J Nucl Med, 2014, 55(1):1229.

McGrath et al., "CD206-targeted Cy3-Manocept (Mano¬Cy3) localizes in nearly all cells present in Kaposi's sarcoma representing an opportunity for dynamic imaging, local staging and a potential for visceral metastasis imaging", Journal of Nuclear Medicine, 2014, 55(1):1681.

Rosol et al., "Intravenous administration (IV) of the CD206-targeted Manocept-Cy3 (Mano-Cy3) to mice with induced rheumatoid arthritis (RA) results in heterogeneous localization of Mano-Cy3 with strong specificity for RA-expressing joints," J Nucl Med, 2014, 55(1):1232.

Vera, David R. et al., "Cy5.5-DTPA-galactosyl-dextran: A fluorescent probe for in vivo measurement of receptor biochemistry". Nuclear medicine and biology. 32. 687-93. 10.1016/j.nucmedbio.2005.04.003.

\* cited by examiner

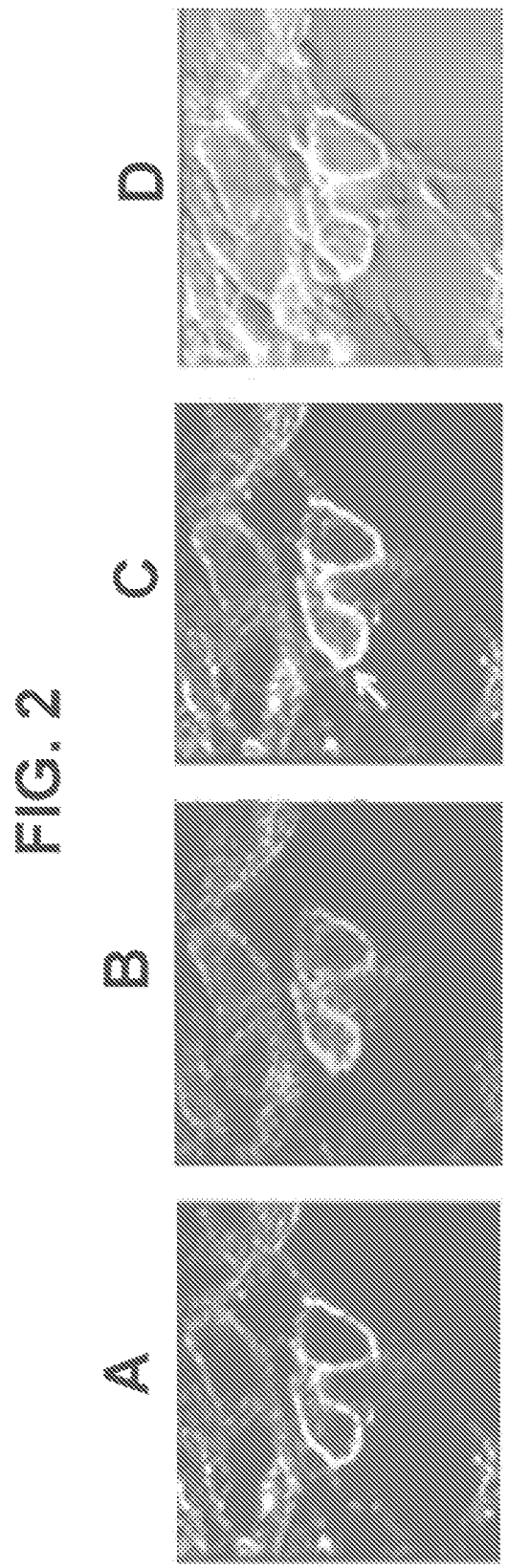

FIG. 3
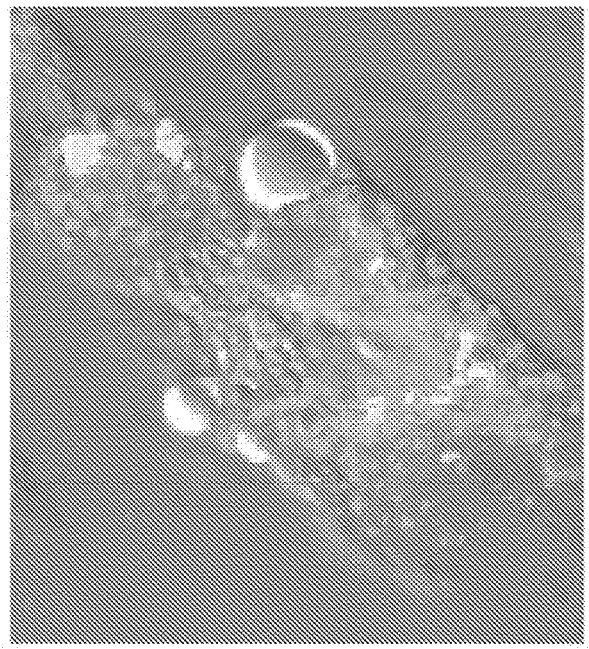
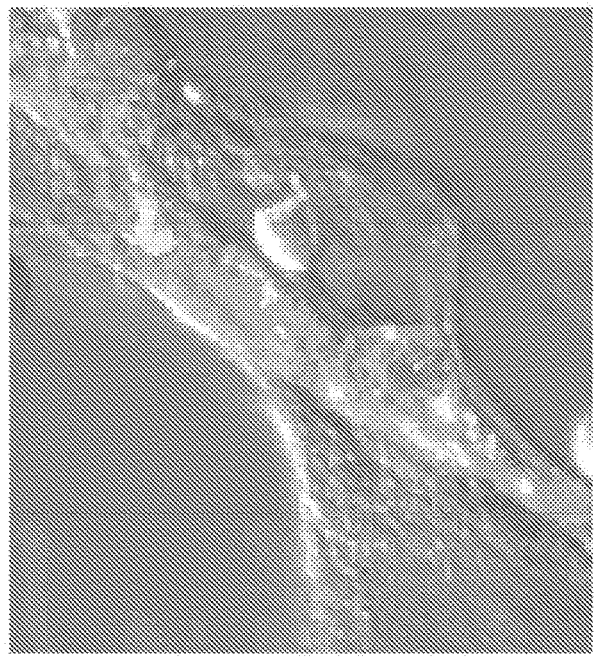
Red: Etanercept-Cy3
Green: GFP-M. tuberculosis
Yellow: Etan

COMPOSITIONS FOR TARGETING MACROPHAGES AND OTHER CD206 HIGH EXPRESSING CELLS AND METHODS OF TREATING AND DIAGNOSIS

CROSS-REFERENCE TO RELATED APPLICATIONS

This application is a U.S. national stage entry of International Patent Application No. PCT/US2015/041019, filed on Jul. 17, 2015, which claims priority to U.S. Provisional Patent Application No. 62/025,991, filed on Jul. 17, 2014, U.S. Provisional Patent Application No. 62/027,193, filed on Jul. 21, 2014, U.S. Provisional Patent Application No. 62/027,220, filed on Jul. 21, 2014, and U.S. Provisional Patent Application No. 62/027,733, filed on Jul. 22, 2014, the entire contents of which are incorporated herein by reference.

BACKGROUND

Tilmanocept is a dextran based drug delivery vehicle. Tilmanocept has been used in the clinics to perform sentinel lymph node mapping. Tilmanocept has a small molecular size (7 nanometers) and carries multiple units of mannose. This mannose component has a high affinity for CD206 which is found in high concentrations on the surface of macrophages, dendritic cells and other cells. By tightly binding to these mannose receptors, Tilmanocept accumulates in lymphatic tissue within minutes and localizes in tumor-draining lymph nodes.

SUMMARY

In one aspect, provided is a compound of Formula (II):

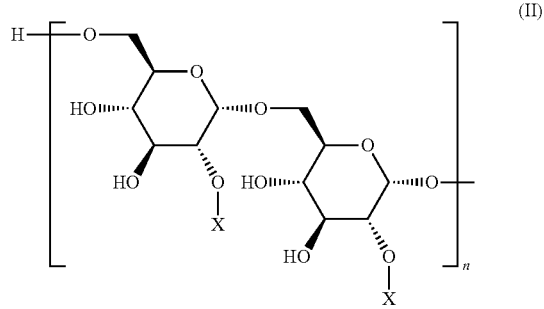

wherein
each X is independently H, $L_1$-A, or $L_2$-R;
each $L_1$ and $L_2$ are independently linkers;
each A independently comprises a therapeutic agent or a detection label or H;
each R independently comprises a CD206 targeting moiety or H;
and
n is an integer greater than zero; and
wherein at least one X is $L_1$-A wherein $L_1$ comprises a hydrazone and at least one X is $L_2$-R.

In another aspect, provided is a method of synthesizing a compound as described above.

BRIEF DESCRIPTION OF THE DRAWINGS

FIG. 2A-2D show representative confocal images (magnification: 160×) showing expression of the CD206 MR (FIG. 2A), tilmanocept binding by the macrophage (FIG. 2B), and co-localization between the MR and tilmanocept in both confocal and phase contrast images (FIGS. 2C and 2D).
FIG. 3 shows binding and internalization of tilmanocept by macrophages.

DETAILED DESCRIPTION

Figure 1A:
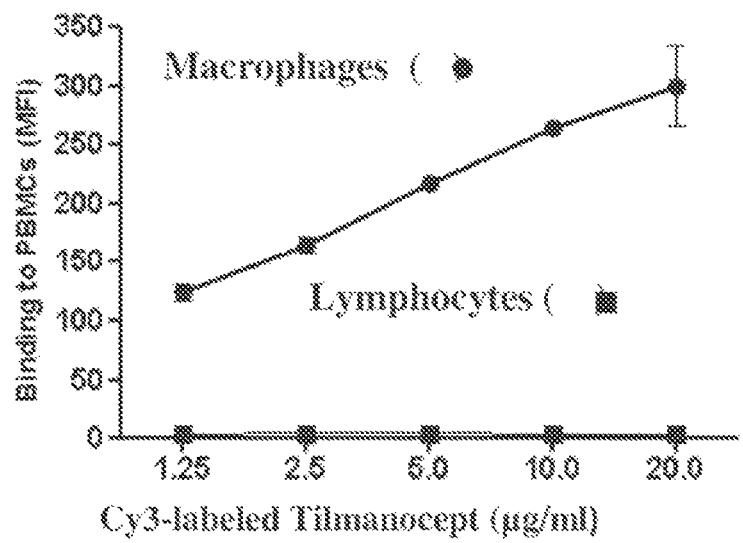
FIG. 1A-1C show tilmanocept binding to macrophages.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Among other things, the present invention is directed compounds and compositions for targeting macrophages and other cells (such as dendritic cells) that express CD-206 using a dextran-based carrier. The present invention also provides methods of making such compounds and compositions. The present invention also provides diagnostic methods and methods of treatment using compounds comprising a dextran-based moiety.

In some embodiments, the present invention provides compounds, compositions and methods for the diagnosis and/or treatment of diseases mediated by CD206-high expressing cells using synthetic macromolecules (e.g., about 2-30 kDa). CD206 is a C-type lectin protein found on macrophages and other cells. These diseases include any condition in which macrophages or other CD206-high expressing cells are involved or recruited, such as those in which the number of macrophages or other CD206-high expressing cells is increased and/or such cells are abnormally localized (e.g., in tumors, affected joints, etc.). Such diseases include immune diseases, autoimmune diseases, inflammatory diseases, and infectious diseases.

Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Perkin Elmer Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the phrase "identified to be in need of treatment for a disorder," or the like, refers to selection of a subject based upon need for treatment of the disorder. For example, a subject can be identified as having a need for treatment of a disorder based upon an earlier diagnosis by a person of skill and thereafter subjected to treatment for the disorder. It is contemplated that the identification can, in one aspect, be performed by a person different from the person making the diagnosis. It is also contemplated, in a further aspect, that the identification can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, intradermal administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, a target receptor (e.g. CD206), or other biological entity together in such a manner that the compound can affect the activity of the target, either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause unacceptable adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The term "pharmaceutically acceptable" describes a material that is not biologically or otherwise undesirable, i.e., without causing an unacceptable level of undesirable biological effects or interacting in a deleterious manner.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

"Alkyl" refers to a saturated aliphatic hydrocarbon including straight chain and branched chain groups. "Alkyl" may be exemplified by groups such as methyl, ethyl, n-propyl, isopropyl, n-butyl and the like. Alkyl groups may be substituted or unsubstituted. More than one substituent may be present. Substituents may also be themselves substituted. When substituted, the substituent group is preferably but not limited to $C_1$-$C_4$ alkyl, aryl, heteroaryl, amino, imino, cyano, halogen, alkoxy or hydroxyl. "$C_1$-$C_4$ alkyl" refers to alkyl groups containing one to four carbon atoms.

"Alkenyl" refers to an unsaturated aliphatic hydrocarbon moiety including straight chain and branched chain groups. Alkenyl moieties must contain at least one alkene. "Alkenyl" may be exemplified by groups such as ethenyl, n-propenyl, isopropenyl, n-butenyl and the like. Alkenyl groups may be substituted or unsubstituted. More than one substituent may be present. When substituted, the substituent group is preferably alkyl, halogen or alkoxy. Substituents may also be themselves substituted. Substituents can be placed on the alkene itself and also on the adjacent member atoms or the alkenyl moiety. "$C_2$-$C_4$ alkenyl" refers to alkenyl groups containing two to four carbon atoms.

"Alkynyl" refers to an unsaturated aliphatic hydrocarbon moiety including straight chain and branched chain groups. Alkynyl moieties must contain at least one alkyne. "Alkynyl" may be exemplified by groups such as ethynyl, propynyl, n-butynyl and the like. Alkynyl groups may be substituted or unsubstituted. More than one substituent may be present. When substituted, the substituent group is preferably alkyl, amino, cyano, halogen, alkoxyl or hydroxyl. Substituents may also be themselves substituted. Substituents are not on the alkyne itself but on the adjacent member atoms of the alkynyl moiety. "$C_2$-$C_4$ alkynyl" refers to alkynyl groups containing two to four carbon atoms.

"Acyl" or "carbonyl" refers to the group —C(O)R wherein R is alkyl; alkenyl; alkynyl, aryl, heteroaryl, carbocyclic, heterocarbocyclic; $C_1$-$C_4$ alkyl aryl or $C_1$-$C_4$ alkyl heteroaryl. $C_1$-$C_4$ alkylcarbonyl refers to a group wherein the carbonyl moiety is preceded by an alkyl chain of 1-4 carbon atoms.

"Alkoxy" refers to the group —O—R wherein R is acyl, alkyl alkenyl, alkyl alkynyl, aryl, carbocyclic; heterocarbocyclic; heteroaryl, $C_1$-$C_4$ alkyl aryl or $C_1$-$C_4$ alkyl heteroaryl.

"Amino" refers to the group —NR'R' wherein each R' is, independently, hydrogen, amino, hydroxyl, alkoxyl, alkyl, aryl, cycloalkyl, heterocycloalkyl, heteroaryl, $C_1$-$C_4$ alkyl aryl or $C_1$-$C_4$ alkyl heteroaryl. The two R' groups may themselves be linked to form a ring. The R' groups may themselves be further substituted, in which case the group also known as guanidinyl is specifically contemplated under the term 'amino".

"Aryl" refers to an aromatic carbocyclic group. "Aryl" may be exemplified by phenyl. The aryl group may be substituted or unsubstituted. More than one substituent may be present. Substituents may also be themselves substituted. When substituted, the substituent group is preferably but not limited to heteroaryl; acyl, carboxyl, carbonylamino, nitro, amino, cyano, halogen, or hydroxyl.

"Carboxyl" refers to the group —C(=O)O—$C_1$-$C_4$ alkyl.

"Carbonyl" refers to the group —C(O)R wherein each R is, independently, hydrogen, alkyl, aryl, cycloalkyl; heterocycloalkyl; heteroaryl, $C_1$-$C_4$ alkyl aryl or $C_1$-$C_4$ alkyl heteroaryl.

"Carbonylamino" refers to the group —C(O)NR'R' wherein each R' is, independently, hydrogen, alkyl, aryl, cycloalkyl; heterocycloalkyl; heteroaryl, $C_1$-$C_4$ alkyl aryl or $C_1$-$C_4$ alkyl heteroaryl. The two R' groups may themselves be linked to form a ring.

"$C_1$-$C_4$ alkyl aryl" refers to $C_1$-$C_4$ alkyl groups having an aryl substituent such that the aryl substituent is bonded through an alkyl group. "$C_1$-$C_4$ alkyl aryl" may be exemplified by benzyl.

"$C_1$-$C_4$ alkyl heteroaryl" refers to $C_1$-$C_4$ alkyl groups having a heteroaryl substituent such that the heteroaryl substituent is bonded through an alkyl group.

"Carbocyclic group" or "cycloalkyl" means a monovalent saturated or unsaturated hydrocarbon ring. Carbocyclic groups are monocyclic, or are fused, spiro, or bridged bicyclic ring systems. Monocyclic carbocyclic groups contain 3 to 10 carbon atoms, preferably 4 to 7 carbon atoms, and more preferably 5 to 6 carbon atoms in the ring. Bicyclic carbocyclic groups contain 8 to 12 carbon atoms, preferably 9 to 10 carbon atoms in the ring. Carbocyclic groups may be substituted or unsubstituted. More than one substituent may be present. Substituents may also be themselves substituted. Preferred carbocyclic groups include cyclopropyl, cyclobutyl, cyclopentyl, cyclohexyl, cyclohexenyl, and cycloheptyl. More preferred carbocyclic groups include cyclopropyl and cyclobutyl. The most preferred carbocyclic group is cyclopropyl. Carbocyclic groups are not aromatic.

"Halogen" refers to fluoro, chloro, bromo or iodo moieties. Preferably, the halogen is fluoro, chloro, or bromo.

"Heteroaryl" or "heteroaromatic" refers to a monocyclic or bicyclic aromatic carbocyclic radical having one or more heteroatoms in the carbocyclic ring. Heteroaryl may be substituted or unsubstituted. More than one substituent may be present. When substituted, the substituents may themselves be substituted. Preferred but non limiting substituents are aryl, $C_1$-$C_4$ alkylaryl, amino, halogen, hydroxy, cyano, nitro, carboxyl, carbonylamino, or $C_1$-$C_4$ alkyl. Preferred heteroaromatic groups include tetrazoyl, triazolyl, thienyl, thiazolyl, purinyl, pyrimidyl, pyridyl, and furanyl. More preferred heteroaromatic groups include benzothiofuranyl; thienyl, furanyl, tetrazoyl, triazolyl, and pyridyl.

"Heteroatom" means an atom other than carbon in the ring of a heterocyclic group or a heteroaromatic group or the chain of a heterogeneous group. Preferably, heteroatoms are selected from the group consisting of nitrogen, sulfur, and oxygen atoms. Groups containing more than one heteroatom may contain different heteroatoms.

"Heterocarbocyclic group" or "heterocycloalkyl" or "heterocyclic" means a monovalent saturated or unsaturated hydrocarbon ring containing at least one heteroatom. Heterocarbocyclic groups are monocyclic, or are fused, spiro, or bridged bicyclic ring systems. Monocyclic heterocarbocyclic groups contain 3 to 10 carbon atoms, preferably 4 to 7 carbon atoms, and more preferably 5 to 6 carbon atoms in the ring. Bicyclic heterocarbocyclic groups contain 8 to 12 carbon atoms, preferably 9 to 10 carbon atoms in the ring. Heterocarbocyclic groups may be substituted or unsubstituted. More than one substituent may be present. Substituents may also be themselves substituted. Preferred heterocarbocyclic groups include epoxy, tetrahydrofuranyl, azacyclopentyl, azacyclohexyl, piperidyl, and homopiperidyl. More preferred heterocarbocyclic groups include piperidyl, and homopiperidyl. The most preferred heterocarbocyclic group is piperidyl. Heterocarbocyclic groups are not aromatic.

"Hydroxy" or "hydroxyl" means a chemical entity that consists of —OH. Alcohols contain hydroxy groups. Hydroxy groups may be free or protected. An alternative name for hydroxy is hydroxyl.

"Member atom" means a carbon, nitrogen, oxygen or sulfur atom. Member atoms may be substituted up to their normal valence. If substitution is not specified the substituents required for valency are hydrogen.

"Ring" means a collection of member atoms that are cyclic. Rings may be carbocyclic, aromatic, or heterocyclic or heteroaromatic, and may be substituted or unsubstituted, and may be saturated or unsaturated. More than one substituent may be present. Ring junctions with the main chain may be fused or spirocyclic. Rings may be monocyclic or bicyclic. Rings contain at least 3 member atoms and at most 10 member atoms. Monocyclic rings may contain 3 to 7 member atoms and bicyclic rings may contain from 8 to 12 member atoms. Bicyclic rings themselves may be fused or spirocyclic.

"Thioalkyl" refers to the group —S— alkyl.

"Sulfonyl" refers to the —S(O)$_2$R' group wherein R' is alkoxy, alkyl, aryl, carbocyclic, heterocarbocyclic; heteroaryl, $C_1$-$C_4$ alkyl aryl or $C_1$-$C_4$ alkyl heteroaryl.

"Sulfonylamino" refers to the —S(O)$_2$NR'R' group wherein each R' is independently alkyl, aryl, heteroaryl, $C_1$-$C_4$ alkyl aryl or $C_1$-$C_4$ alkyl heteroaryl.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental Volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Compounds

In some embodiments, the present invention provides a compound comprising a dextran-based moiety or backbone having one or more CD206 targeting moieties and one or more therapeutic agents attached thereto. The dextran-based moiety generally comprises a dextran backbone similar to that described in U.S. Pat. No. 6,409,990 (the '990 patent), which is incorporated herein by reference. Thus, the backbone comprises a plurality of glucose moieties (i.e., residues) primarily linked by α-1,6 glycosidic bonds. Other linkages such as α-1,4 and/or α-1,3 bonds may also be present. In some embodiments, not every backbone moiety is substituted. In some embodiments, CD206 targeting moieties are attached to between about 10% and about 50% of the glucose residues of the dextran backbone, or between about 20% and about 45% of the glucose residues, or between about 25% and about 40% of the glucose residues. In some embodiments, the dextran-based moiety is about 50-100 kD. The dextran-based moiety may be at least about 50 kD, at least about 60 kD, at least about 70 kD, at least about 80 kD, or at least about 90 kD. The dextran-based moiety may be less than about 100 kD, less than about 90 kD, less than about 80 kD, less than about 70 kD, or less than about 60 kD. Alternatively, in some embodiments, the dextran backbone has a MW of between about 1 and about 50 kDa, while in other embodiments the dextran backbone has a MW of between about 5 and about 25 kDa. In still other embodiments, the dextran backbone has a MW of between about 8 and about 15 kDa, such as about 10 kDa. While in other embodiments the dextran backbone has a MW of between about 1 and about 5 kDa, such as about 2 kDa.

By way of one example, carrier molecules having smaller MW dextran backbones may be appropriate for instances where the molecule is desired to cross the blood-brain barrier, or when reduced residence time is desired (i.e., the duration of binding to CD206 is reduced). Carrier molecules having larger MW dextran backbones may be appropriate for instances where increased residence time is desired (i.e., the duration of binding to CD206 is increased). In still other embodiments, carrier molecules having smaller MW dextran backbones (e.g., about 1 to about 5 kDa) may be employed when more efficient receptor substrates are attached to the dextran backbone (e.g., branched mannose moieties, as described below). More efficient receptor substrates will bind to CD206 for longer durations and/or more effectively, thus allowing for the use of smaller dextran backbones.

In some embodiments, the CD206 targeting moiety is selected from, but not limited to, mannose, fucose, and n-acetylglucosamine. In some embodiments, the targeting moieties are attached to between about 10% and about 50% of the glucose residues of the dextran backbone, or between about 20% and about 45% of the glucose residues, or between about 25% and about 40% of the glucose residues. (It should be noted that the MWs referenced herein, as well as the number and degree of conjugation of receptor substrates, leashes, and diagnostic/therapeutic moieties attached to the dextran backbone refer to average amounts for a given quantity of carrier molecules, since the synthesis techniques will result in some variability.)

In some embodiments, the one or more CD206 targeting moieties and one or more therapeutic agents (or drugs) and/or detection labels are attached to the dextran-based moiety through a linker. The linker may be attached at from about 50% to about 100% of the backbone moieties or about 70% to about 90%. The linkers may be the same or different. In some embodiments, the linker is an amino-terminated linker. In some embodiments, the linkers may comprise —O(CH$_2$)$_3$S(CH$_2$)$_2$NH—. In some embodiments, the linker may be a chain of from 1 to 20 member atoms selected from carbon, oxygen, sulfur, nitrogen and phosphorus. The linker may be a straight chain or branched. The linker may also be substituted with one or more substituents including, but not limited to, halo groups, perfluoroalkyl groups, perfluoroalkoxy groups, alkyl groups, such $C_{1-4}$ alkyl, alkenyl groups, such as $C_{1-4}$ alkenyl, alkynyl groups, such as $C_{1-4}$ alkynyl, hydroxy groups, oxo groups, mercapto groups, alkylthio groups, alkoxy groups, nitro groups, azidealkyl groups, aryl or heteroaryl groups, aryloxy or heteroaryloxy groups, aralkyl or heteroaralkyl groups, aralkoxy or heteroaralkoxy groups, HO—(C═O)— groups, heterocylic groups, cycloalkyl groups, amino groups, alkyl- and dialkylamino groups, carbamoyl groups, alkylcarbonyl groups, alkylcarbonyloxy groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups, —NH—NH$_2$; ═N—H; ═N-alkyl; —SH; —S-alkyl; —NH—C(O)—; —NH—C(═N)— and the like. Other suitable linkers would be known to one of ordinary skill in the art.

In some embodiments, the one or more therapeutic agent is attached via a biodegradable linker. In some embodiments, the biodegradable linker is acid sensitive, such as a hydrazone linker. The use of an acid sensitive linker enables the drug to be transported into the cell and allows for the release of the drug substantially inside of the cell.

The therapeutic agent may be any compound known to be useful for the treatment of a macrophage-mediated disease. Therapeutic agents include, but are not limited to, chemotherapeutic agents, such as doxorubicin; anti-infective agents, such as antibiotics (e.g. tetracycline, streptomycin, and isoniazid), anti-virals, anti-fungals, and anti-parasitics; immunological adjuvants; steroids; nucleotides, such as DNA, RNA, RNAi, siRNA, CpG or Poly (I:C); peptides; proteins; or metals such as silver, gallium or gadolinium.

In certain embodiments, the therapeutic agent is an anti-microbial drug selected from the group comprising or consisting of: an antibiotic; an anti-tuberculosis antibiotic (such as isoniazid, streptamycin, or ethambutol); an anti-viral or anti-retroviral drug, for example an inhibitor of reverse transcription (such as zidovudin) or a protease inhibitor (such as indinavir); drugs with effect on leishmaniasis (such as Meglumine antimoniate). In certain embodiments, the therapeutic agent is an anti-microbial active, such as amoxicillin, ampicillin, tetracyclines, aminoglycosides (e.g., streptomycin), macrolides (e.g., erythromycin and its relatives), chloramphenicol, ivermectin, rifamycins and polypeptide antibiotics (e.g., polymyxin, bacitracin) and zwittermicin. In certain embodiments, the therapeutic agent is selected from isoniazid, doxorubicin, streptomycin, and tetracycline.

In some embodiments, the therapeutic agent comprises a high energy killing isotope which has the ability to kill macrophages and tissue in the surrounding macrophage environment. Suitable radioisotopes include: $^{210/212/213/214}$Bi, $^{131/140}$Ba, $^{11/14}$C, $^{51}$Cr, $^{67/68}$Ga, $^{153}$Gd, $^{99m}$Tc, $^{88/90/91}$Y, $^{123/124/125/131}$I, $^{111/115m}$In, $^{18}$F, $^{105}$Rh, $^{153}$Sm, $^{67}$Cu, $^{166}$Ho, $^{177}$Lu, $^{186}$Re and $^{188}$Re, $^{32/33}$P, $^{46/47}$Sc, $^{72/75}$Se, $^{35}$S, $^{182}$Ta, $^{123m/127/129/132}$Te$^{65}$, Zn and $^{89/95}$Zr.

In other embodiments, the therapeutic agent comprises a non-radioactive species selected from, but not limited to, the group consisting of: Bi, Ba, Mg, Ni, Au, Ag, V, Co, Pt, W, Ti, Al, Si, Os, Sn, Br, Mn, Mo, Li, Sb, F, Cr, Ga, Gd, I, Rh, Cu, Fe, P, Se, S, Zn and Zr.

In still further embodiments, the therapeutic agent is selected from the group consisting of cytostatic agents, alkylating agents, antimetabolites, anti-proliferative agents, tubulin binding agents, hormones and hormone antagonists, anthracycline drugs, vinca drugs, mitomycins, bleomycins, cytotoxic nucleosides, pteridine drugs, diynenes, podophyllotoxins, toxic enzymes, and radiosensitizing drugs. By way of more specific example, the therapeutic agent is selected from the group consisting of mechlorethamine, triethylenephosphoramide, cyclophosphamide, ifosfamide, chlorambucil, busulfan, melphalan, triaziquone, nitrosourea compounds, adriamycin, carminomycin, daunorubicin (daunomycin), doxorubicin, isoniazid, indomethacin, gallium(III), 68gallium(III), aminopterin, methotrexate, methopterin, mithramycin, streptonigrin, dichloromethotrexate, mitomycin C, actinomycin-D, porfiromycin, 5-fluorouracil, floxuridine, ftorafur, 6-mercaptopurine, cytarabine, cytosine arabinoside, podophyllotoxin, etoposide, etoposide phosphate, melphalan, vinblastine, vincristine, leurosidine, vindesine, leurosine, taxol, taxane, cytochalasin B, gramicidin D, ethidium bromide, emetine, tenoposide, colchicin, dihydroxy anthracin dione, mitoxantrone, procaine, tetracaine, lidocaine, propranolol, puromycin, ricin subunit A, abrin, diptheria toxin, botulinum, cyanginosins, saxitoxin, shigatoxin, tetanus, tetrodotoxin, trichothecene, verrucologen, corticosteroids, progestins, estrogens, antiestrogens, androgens, aromatase inhibitors, calicheamicin, esperamicins, and dynemicins.

In embodiments wherein the therapeutic agent is a hormone or hormone antagonist, the therapeutic agent may be selected from the group consisting of prednisone, hydroxyprogesterone, medroprogesterone, diethylstilbestrol, tamoxifen, testosterone, and aminogluthetimide.

In embodiments wherein the therapeutic agent is a prodrug, the therapeutic agent may be selected from the group consisting of phosphate-containing prodrugs, thiophosphate-containing prodrugs, sulfate containing prodrugs, peptide containing prodrugs, (-lactam-containing prodrugs, optionally substituted phenoxyacetamide-containing prodrugs, optionally substituted phenylacetamide-containing prodrugs, 5-fluorocytosinem, and 5-fluorouridine prodrugs that can be converted to the more active cytotoxic free drug.

In some embodiments, the dextran-based moiety having at least one CD206 targeting moiety attached thereto is a compound of Formula (I):

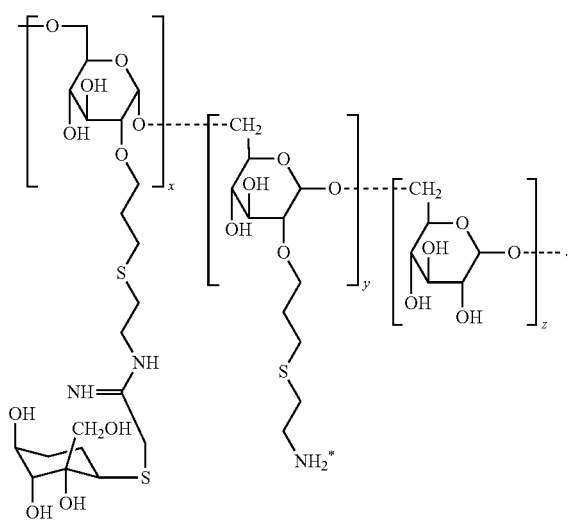

wherein the * indicates the point at which the therapeutic agent is attached. In certain embodiments, the therapeutic agent is attached via a linker.

In embodiments, the compound of the present invention is a compound of Formula (II):

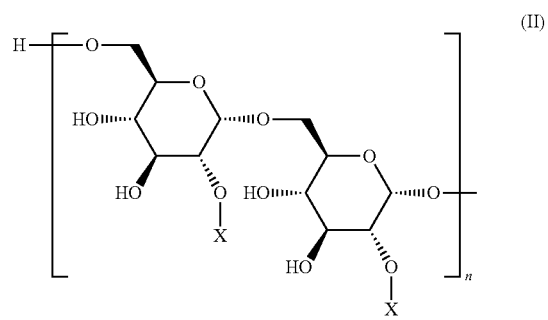

wherein each X is independently H, $L_1$-A, or $L_2$-R;

each $L_1$ and $L_2$ are independently linkers;

each A independently comprises a therapeutic agent or a detection label or H;

each R independently comprises a CD206 targeting moiety or H;

and n is an integer greater than zero; and wherein at least one X is $L_1$-A wherein $L_1$ comprises a hydrazone and at least one X is $L_2$-R.

In certain embodiments, $L_1$ is a linker as described above. In certain embodiments, $L_2$ is a linker as described above.

Synthesis

The compounds of this invention can be prepared by employing reactions as shown in the disclosed schemes, in addition to other standard manipulations that are known in the literature, exemplified in the experimental sections or clear to one skilled in the art. The following examples are provided so that the invention might be more fully understood, are illustrative only, and should not be construed as limiting. For clarity, examples having a fewer substituent can be shown where multiple substituents are allowed under the definitions disclosed herein.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed compositions, kits, and uses.

The compounds of the present invention may be synthesized by any number of ways known to one of ordinary skill in the art. For example, linker 2 can be synthesized by opening succinic anhydride ring by tert-butyl carbazate. The resulting carboxylic acid is converted to the corresponding N-hydroxy succinimide (NHS) ester using EDC coupling reagent. Tilmanocept is then functionalized with linker 2 by forming an amide linkage. Then, the Boc protecting group can be removed under dilute acidic condition (typically 30-40% trifluoroacetic acid in DMSO) to obtain 4. Dilute acidic condition is required to avoid any unwanted cleavage of the glycosidic linkage present in dextran backbone. The resulting functionalized tilmanocept can purified by size exclusion filtration.

Scheme 1: Synthetic route A for the modification of tilmanocept

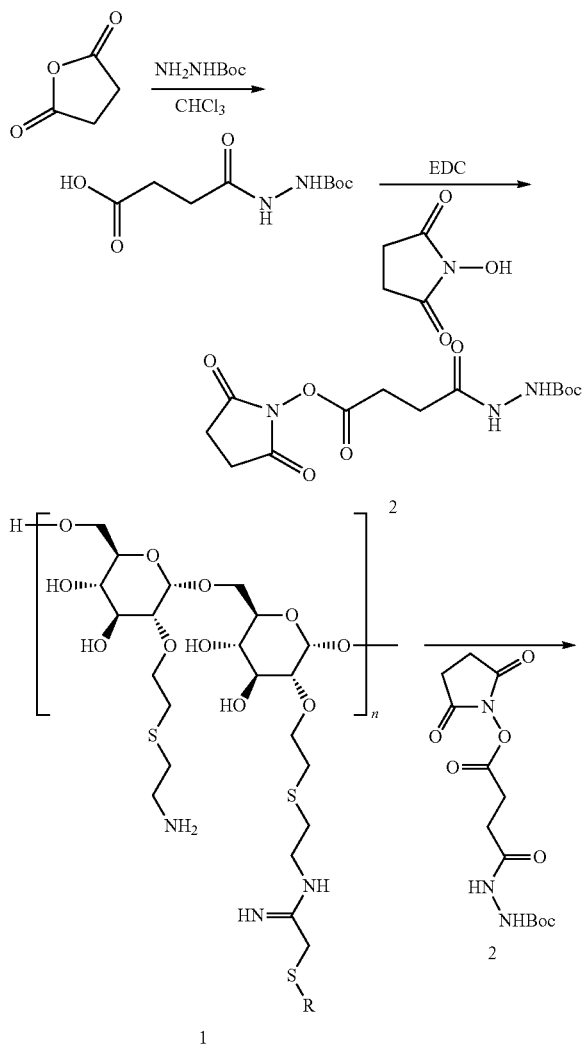

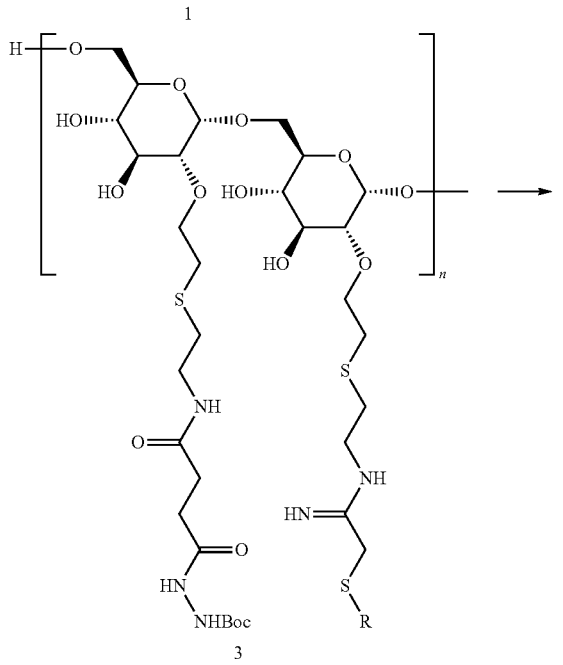

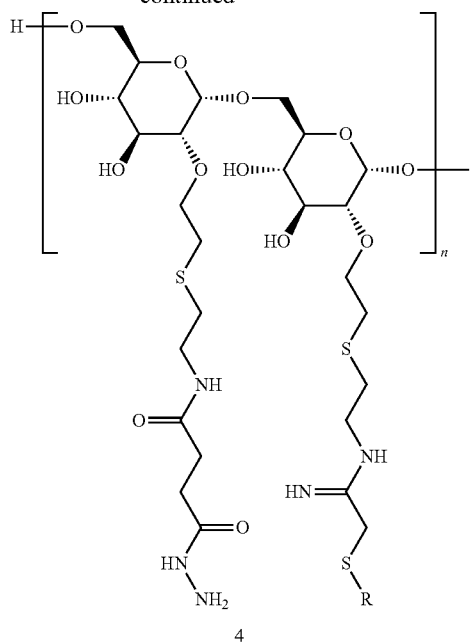

R = mannose

Alternatively, compounds according to the present invention may be synthesized according to Scheme 2. Free primary amine groups of tilmanocept can be reacted with an excess of lactone under anhydrous condition. Unreacted lactone can be removed under reduced pressure to obtain modified tilmanocept 6. The corresponding hydrazine derivative 7 can be prepared by reductive amination reaction using sodium cyanoborohydride or sodium triacetoxy borohydride as the reducing agent.

Scheme 2: Synthetic route B for the modification of tilmanocept

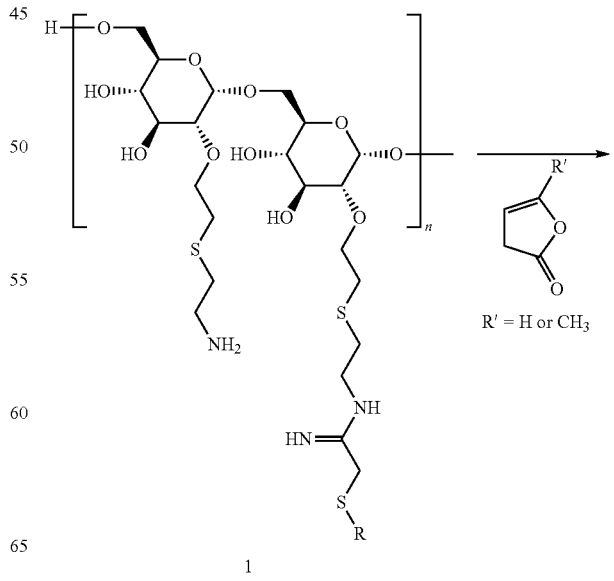

R' = H or CH$_3$

17

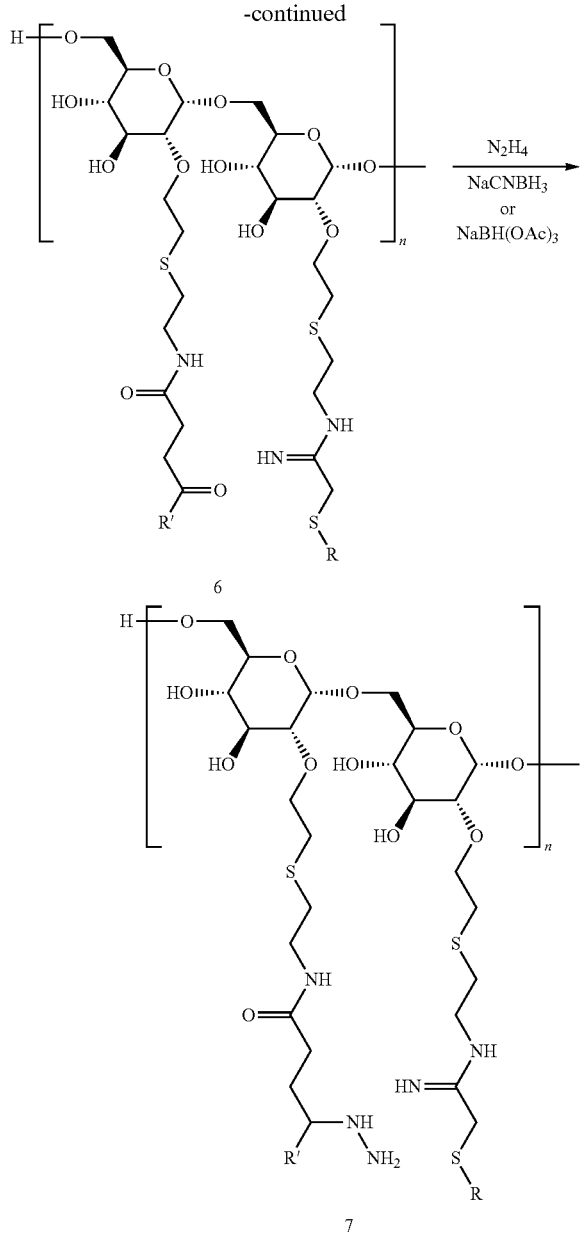

R = mannose

18

The conjugation of oxo-containing therapeutic agents to tilmanocept derivatives 4 or 7 can be as is shown in Scheme 3. Tilmanocept derivative 4 or 7 can be conjugated to doxorubicin by formation of hydrazone linkage under anhydrous acidic condition or aqueous acidic conditions. Unconjugated therapeutic agent can be removed (e.g. by size exclusion chromatography or dialyzation) to obtain the pure conjugated tilmanocept.

Scheme 3: Conjugation of doxorubicin to tilmanocept derivatives intermediate 4
or
intermediate 7

+

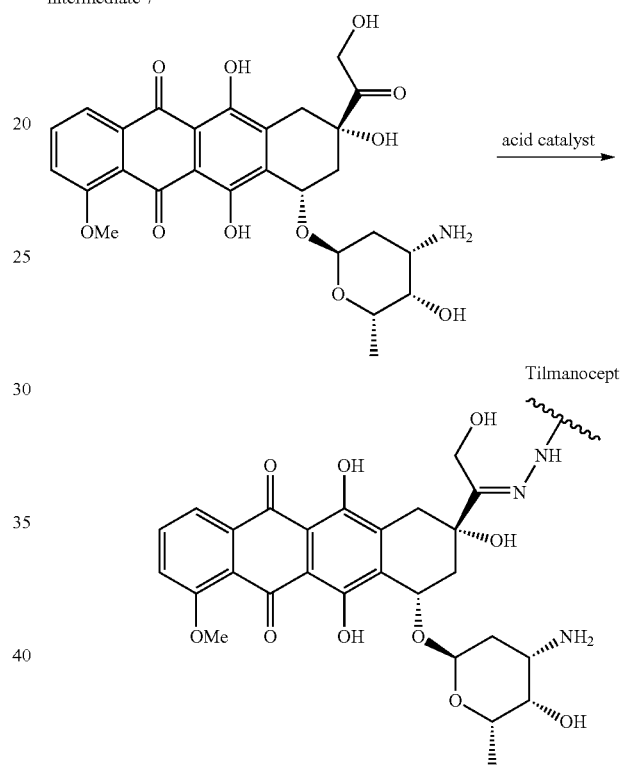

Amine-containing therapeutic agents may be conjugated to dextran-containing compounds, such as tilmanocept, according to Scheme 4. The basic reaction between a primary amine and the lactone are shown in Scheme 4.

Scheme 4.

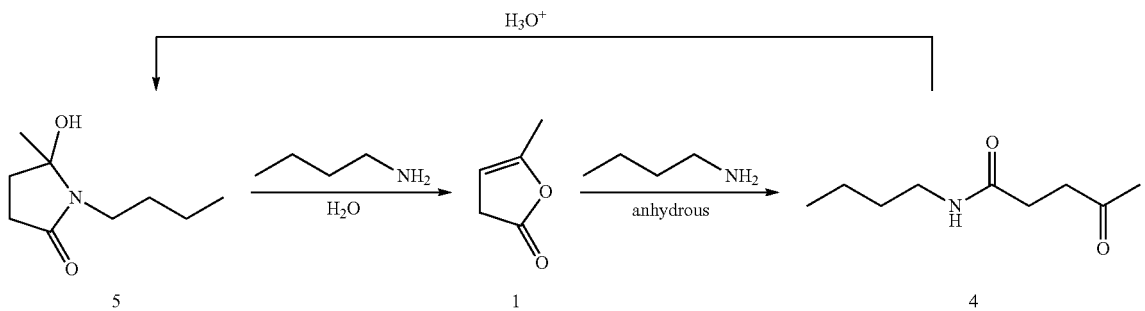

Scheme 5.

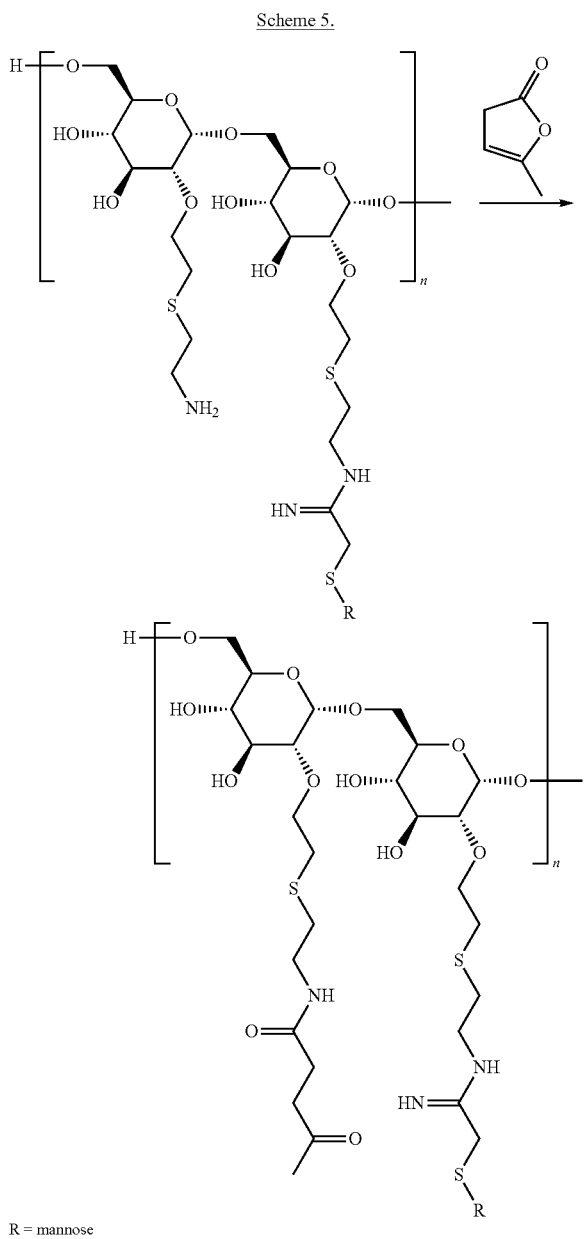

R = mannose

One of ordinary skill in the art would recognize other ways to synthesize the compounds of the present invention.

Pharmaceutical Compositions

In one aspect, the invention relates to pharmaceutical compositions comprising the disclosed compounds and products of disclosed methods. That is, a pharmaceutical composition can be provided comprising an effective amount of at least one disclosed compound, at least one product of a disclosed method, or a pharmaceutically acceptable salt, solvate, hydrate, or polymorph thereof, and a pharmaceutically acceptable carrier. In one aspect, the invention relates to pharmaceutical compositions comprising a pharmaceutically acceptable carrier and an effective amount of at least one disclosed compound; or a pharmaceutically acceptable salt, hydrate, solvate, or polymorph thereof.

In a further aspect, the effective amount is a therapeutically effective amount. In a still further aspect, the effective amount is a prophylactically effective amount. In a still further aspect, the pharmaceutical composition comprises a compound that is a product of a disclosed method of making.

In a further aspect, the pharmaceutical composition comprises a disclosed compound. In a yet further aspect, the pharmaceutical composition comprises a product of a disclosed method of making.

In one aspect, the pharmaceutical composition is used to treat a mammal. In a yet further aspect, the mammal is a human. In a further aspect, the mammal has been diagnosed with a need for treatment of the disorder prior to the administering step. In a further aspect, the mammal has been identified to be in need of treatment of the disorder.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, intradermal and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids," includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as lyophilized powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

Diagnostic Methods

Diagnostic methods are disclosed for in vivo detection of diseases or conditions using the disclosed compounds.

In certain embodiments, the disclosed compounds include a detection label in addition to the therapeutic agent. As used herein, the term "detectable label or moiety" means an atom, isotope, or chemical structure which is: (1) capable of attachment to the carrier molecule; (2) non-toxic to humans or other mammalian subjects; and (3) provides a directly or indirectly detectable signal, particularly a signal which not only can be measured but whose intensity is related (e.g., proportional) to the amount of the detectable moiety. The signal may be detected by any suitable means, including spectroscopic, electrical, optical, magnetic, auditory, radio signal, or palpation detection means.

Detection labels include, but are not limited to, fluorescent molecules (a.k.a. fluorochromes and fluorophores), chemiluminescent reagents (e.g., luminol), bioluminescent reagents (e.g., luciferin and green fluorescent protein (GFP)), metals (e.g., gold nanoparticles), and radioactive isotopes (radioisotopes). Suitable detection labels can be selected based on the choice of imaging method. For example, the detection label can be a near infrared fluorescent dye for optical imaging, a Gadolinium chelate for MRI imaging, a radionuclide for PET or SPECT imaging, or a gold nanoparticle for CT imaging.

Detection labels can be selected from, for example, a radionuclide, a radiological contrast agent, a paramagnetic ion, a metal, a fluorescent label, a chemiluminescent label, an ultrasound contrast agent, a photoactive agent, or a combination thereof. Non-limiting examples of detectable labels include a radionuclide such as $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{120}$I, $^{123}$I, $^{124}$I, $^{125}$I, $^{131}$I, $^{154-158}$Gd $^{32}$P, $^{11}$C, $^{13}$N, $^{15}$O, $^{186}$Re, $^{188}$R, $^{51}$Mn, $^{52m}$Mn $^{55}$Co, $^{72}$As, $^{75}$Br, $^{76}$Br, $^{82m}$Rb, $^{83}$Sr, $^{117m}$Sn or other gamma-, beta-, or positron-emitters. Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III), Ultrasound contrast agents may comprise liposomes, such as gas-filled liposomes.

Other suitable labels include, for example, fluorescent labels (such as fluorescein, isothiocyanate, rhodamine, phycoerythrin, phycocyanin, allophycocyanin, o-phthaldehyde, and fluorescamine and fluorescent metals such as Eu or others metals from the lanthanide series), near IR dyes, quantum dots, phosphorescent labels, chemiluminescent labels or bioluminescent labels (such as luminal, isoluminol, theromatic acridinium ester, imidazole, acridinium salts, oxalate ester, dioxetane or GFP and its analogs), radioisotopes, metals, metals chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels include moieties that can be detected using NMR or ESR spectroscopy. Such labeled molecules may, for example, be used for in vitro, in vivo or in situ assays (including immunoassays known per se such as ELISA, RIA, EIA and other "sandwich assays," etc.) as well as in vivo diagnostic and imaging purposes, depending on the choice of the specific label. Another modification may involve the introduction of a chelating group, for example, to chelate one of the metals or metallic cations referred to above. Suitable chelating groups, for example, include, without limitation, diethyl-enetriaminepentaacetic acid (DTPA) or ethylenediaminetetraacetic acid (EDTA). Yet another modification may comprise the introduction of a functional group that is one part of a specific binding pair, such as the biotin-(strept) avidin binding pair. Such a functional group may be used to link a disclosed compound to a protein, polypeptide or chemical compound that is bound to the other half of the binding pair, i.e., through formation of the binding pair. For example, such a conjugated molecule may be used as a reporter, for example, in a diagnostic system where a detectable signal-producing agent is conjugated to avidin or streptavidin.

Optical Imaging

The disclosed compounds can include a detectable label useful for optical imaging. A number of approaches can be used for optical imaging. The various methods depend upon fluorescence, bioluminescence, absorption or reflectance as the source of contrast. Fluorophores are compounds or moieties that absorb energy of a specific wavelength and re-emit energy at a different (but equally specific) wavelength. In certain embodiments, the detectable label is a near-infrared (NIR) fluorophore. Suitable NIRs include, but are not limited to, VivoTag-S® 680 and 750, Kodak X-SIGHT Dyes and Conjugates, DyLight 750 and 800 Fluors, Cy 5.5 and 7 Fluors, Alexa Fluor 680 and 750 Dyes, and IRDye 680 and 800CW Fluors. In certain embodiments, Quantum dots, with their photostability and bright emissions, can also be used with optical imaging.

Nuclear Medicine Imaging

The disclosed compounds can include a detectable label (e.g., a radionuclide) useful for nuclear medicine imaging. Nuclear medicine imaging involves the use and detection of radioisotopes in the body. Nuclear medicine imaging techniques include scintigraphy, single photon emission computed tomography (SPECT), and positron emission tomography (PET). In these techniques, radiation from the radioisotopes can be captured by a gamma camera to form two-dimensional images (scintigraphy) or 3-dimensional images (SPECT and PET).

Radioisotopes that can be incorporated into or attached directly to the disclosed compounds include, but are not limited to, tritium, $^{11}$C, $^{13}$N, $^{14}$C, $^{15}$O, $^{18}$Fl, $^{62}$Cu, $^{64}$Cu, $^{67}$Cu, $^{68}$Ga, $^{76}$Br, $^{82}$Rb, $^{90}$Y, $^{99m}$Tc, $^{111}$In, $^{123}$I, $^{124}$I, $^{125}$I, $^{131}$I, $^{153}$Sm, $^{201}$Tl, $^{186}$Re, $^{188}$Re, $^{117m}$Sn and $^{212}$Bi. In certain embodiments, the radioisotope is attached to a disclosed compound by halogenation. Radionuclides used in PET scanning are typically isotopes with short half-lives. Typical isotopes include $^{11}$C, $^{13}$N, $^{15}$O, $^{18}$F, $^{64}$Cu, $^{62}$Cu, $^{124}$I, $^{76}$Br, $^{82}$Rb and $^{68}$Ga, with $^{18}$F being the most clinically utilized.

Gamma radiation from radioisotopes can be detected using a gamma particle detection device. In some embodiments, the gamma particle detection device is a Gamma Finder® device (SenoRx, Irvine Calif.). In some embodiments, the gamma particle detection device is a Neoprobe® GDS gamma detection system (Dublin, Ohio).

Positron emission tomography is a nuclear medicine imaging technique which produces a three-dimensional image or picture of functional processes in the body. Some agents used for PET imaging provide information about tissue metabolism or some other specific molecular activity. Commonly used agents or potential agents that can be used as detectable agents include, but are not limited to: $^{64}$Cu diacetyl-bis(N$^{4}$-methylthiosemicarbazone); $^{18}$F-fluorodeoxyglucose (FDG); $^{18}$F-fluoride; 3'-deoxy-3'[$^{18}$F]fluorothymidine (FLT); $^{18}$F-fluoromisonidazole; Gallium; Technetium-99m; and Thallium. Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoerythrin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

A number of trivalent metal radionuclides have physical properties suitable for radioisotope imaging (e.g., indium-111 ($^{111}$In) gallium-67/68 ($^{67/68}$Ga) and yttrium-86 ($^{86}$Y)) or for targeted radionuclide therapy (e.g., $^{90}$Y and lutetium-177 ($^{177}$Lu)). Diethylenetriaminepentaacetic acid (DTPA) and/or 1,4,7,10-tetraazacyclododecane-1,4,7,10-tetraacetic acid (DOTA; CAS 60239-18-1) can be used (see Choe and Lee, 2007, Current Pharmaceutical Design, 13:17-31; Li et al., 2007, J. Nuclear Medicine, "$^{64}$Cu-Labeled Tetrameric and Octameric RGD Peptides for Small-Animal PET of Tumor avb3 Integrin Expression", 48:1162-1171; Nahrendorf et al, 2009, JACC Cardiovasc. Imaging, 2:10:1213-1222; Li et al., 2009, Mol. Cancer Ther., 8:5:1239-1249; Yim et al., 2010, J. Med. Chem., 53:3944-3953; Dijkgraaf et al., 2010, Eur. J. Nucl. Med. Mol. Imaging, published online 21 Sep. 2010; U.S. patent application Ser. No. 10/792,582; Dransfield et al., U.S. Pat. Pub. Nos. US 2010/0261875; U.S. Pat. No. 7,666,979). Of the metals mentioned, the DOTA complexes are more thermodynamically and kinetically stable than the DTPA complexes (see Sosabowski et al., Nature Protocols 1, -972-976 (2006) and Leon-Rodriguez et al., Bioconjugate chemistry, Jan. 3, 2008; 19(2):391-402).

Magnetic Resonance Imaging

The disclosed compounds can be detected via magnetic resonance imaging. MRI has the advantages of having very high spatial resolution and is very adept at morphological imaging and functional imaging. MRI generally has a sensitivity of around $10^{-3}$ mol/L to $10^{-5}$ mol/L. Improvements to increase MR sensitivity include hyperpolarization by increasing magnetic field strength, optical pumping, or dynamic nuclear polarization. There are also a variety of signal amplification schemes based on chemical exchange that increase sensitivity.

Chelating Agents

In some embodiments, a chelating agent may be attached to or incorporated into a disclosed compound, and used to chelate a therapeutic or diagnostic agent, such as a radionuclide. Exemplary chelators include but are not limited to DTPA (such as Mx-DTPA), DOTA, TETA, NETA or NOTA.

Useful chelators include, but are not limited to, DTPA, DO3A, DOTA, EDTA, TETA, EHPG, HBED, NOTA, DOTMA, TETMA, PDTA, TTHA, LICAM, HYNIC, and MECAM. HYNIC is particularly useful for chelating Tc99, another imaging agent of the invention.

Detecting Cancer In Vivo

The disclosed compounds can be used in combination with molecular imaging to detect cancer cells, such as those that have metastasized and therefore spread to another organ or tissue of the body, using an in vivo imaging device. A non-invasive method is therefore provided for detecting cancer cells in a subject that involves administering a pharmaceutical composition containing the disclosed compounds to the subject and then detecting the biodistribution of disclosed compounds using an imaging device. In some embodiments, the pharmaceutical composition is injected into the parenchyma. In other embodiments, the pharmaceutical composition is injected into the circulation.

The disclosed compounds can also be used for intraoperative detection of cancer cells. For example, the disclosed compounds can be used for intraoperative lymphatic mapping (ILM) to trace the lymphatic drainage patterns in a cancer patient to evaluate potential tumor drainage and cancer spread in lymphatic tissue. In these embodiments, the disclosed compounds are injected into the tumor and their movement through the lymphatic system is traced using a molecular imaging device. As another example, the disclosed compounds can be used for intraoperative assessment of, for example, tumor margins and tumor proximal tissues for the presence of cancer cells. This can be useful, for example, in effectively resecting tumors and detecting the spread of cancer proximal to the tumor.

The disclosed methods of imaging to detect cancer cells are referred to herein as non-invasive. By non-invasive is meant that the disclosed compounds can be detected from outside of the subject's body. By this it is generally meant that the signal detection device is located outside of the subject's body. It is understood, however, that the disclosed compounds can also be detected from inside the subject's body or from inside the subject's gastrointestinal tract or from inside the subject's respiratory system and that such methods of imaging are also specifically contemplated. For example, for intraoperative detection, the signal detection device can be located either outside or inside of the subject's body. From this it should be understood that a non-invasive method of imaging can be used along with, at the same time as, or in combination with an invasive procedure, such as surgery.

In some embodiments, the method can be used to diagnose cancer in a subject or detect cancer in a particular organ of a subject. A particularly useful aspect of this method is the ability to search for metastatic cancer cells in secondary tissues or organs, such as lymph nodes, or at or near tumor margins. Therefore, the disclosed methods can be used for assessing lymph node status in patients that have or are suspected of having cancer, such as breast cancer. This avoids the need to biopsy the tissue or organ, e.g., remove a lymph node. In some embodiments, the method involves administering to the patient the disclosed compounds and detecting whether the compounds have bound to cells in a lymph node. In some of these embodiments, the lymph node can be an axillary lymph node (ALN). In other embodiments, the lymph node can be a sentinel lymph node. In further embodiments, both axillary and sentinel lymph nodes can be assessed for binding of the agent to cells in the lymph node.

The method can also be used with other therapeutic or diagnostic methods. For example, the method can also be used during an operation to, for example, guide cancer removal, which is referred to herein as "intraoperative guidance" or "image guided surgery." In a particular embodiment, the method can be used for therapeutic treatment to remove or destroy cancer cells in a patient's lymph nodes. For example, the disclosed compounds can be administered to a patient, and the location of cancerous tissue (e.g., lymph nodes) can be determined and removed using image guided surgery. In another preferred embodiment, the method can be used for therapeutic treatment to prevent positive microscopic margins after tumor resection. For example, the disclosed compounds can be administered to a patient, the location of cancer cells around a tumor can be determined, and the complete tumor removed using image guided surgery. In these embodiments, the physician administers the disclosed compounds to the patient and uses an imaging device to detect the cancer cells, guide resection of tissue, and assure that all of the cancer is removed. In addition, the imaging device can be used post-operatively to determine if any cancer remains or reoccurs.

In some embodiments, the disclosed compounds can be linked to a therapeutic compound. The therapeutic compound or moiety can be one that kills or inhibits cancer cells directly (e.g., cisplatin) or it can be one that can kill or inhibit a cancer cell indirectly (e.g., gold nanoparticles that kill or destroy cancer cells when heated using a light source). If the therapeutic compound or moiety is one that kills or inhibits a cancer cell indirectly, then the method further comprises a step of taking appropriate action to "activate" or otherwise implement the anti-cancer activity of the compound or moiety. In a specific embodiment, the therapeutic compound or moiety attached to the agent can be a gold nanoparticle and following administration to the patient and binding of the agent to cancer cells, the gold nanoparticles are heated, e.g., using a laser light, to kill or destroy the nearby cancer cells (photothermal ablation). For example, in some embodiments, the method involves image guided surgery using the disclosed compounds to detect and resect cancer from a subject followed by the use of the same or different disclosed compounds linked to a therapeutic compound to kill remaining cancer cells.

The cancer of the disclosed methods can be any cell in a subject undergoing unregulated growth. The cancer can be any cancer cell capable of metastasis. For example, the cancer can be a sarcoma, lymphoma, leukemia, carcinoma, blastoma, or germ cell tumor. A representative but non-limiting list of cancers that the disclosed compositions can be used to detect include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

The cancer can be breast cancer. Breast cancers originating from ducts are known as ductal carcinomas, and those originating from lobules that supply the ducts with milk are known as lobular carcinomas. Common sites of breast cancer metastasis include bone, liver, lung and brain.

The cancer can be non-small-cell lung carcinoma (NSCLC). NSCLC is any type of epithelial lung cancer other than small cell lung carcinoma (SCLC). The most common types of NSCLC are squamous cell carcinoma, large cell carcinoma, and adenocarcinoma, but there are several other types that occur less frequently, and all types can occur in unusual histologic variants and as mixed cell-type combinations.

Actions Based on Imaging and Identifications

The disclosed methods include the determination, identification, indication, correlation, diagnosis, prognosis, etc. (which can be referred to collectively as "identifications") of subjects, diseases, conditions, states, etc. based on imagings, measurements, detections, comparisons, analyses, assays, screenings, etc. For example, the disclosed imaging methods allow identification of patients, organs, tissues, etc. having cancer cells, metastasized cancer cells, cancer cells beyond tumor margins, etc. Such identifications are useful for many reasons. For example, and in particular, such identifications allow specific actions to be taken based on, and relevant to, the particular identification made. For example, diagnosis of a particular disease or condition in particular subjects (and the lack of diagnosis of that disease or condition in other subjects) has the very useful effect of identifying subjects that would benefit from treatment, actions, behaviors, etc. based on the diagnosis. For example, treatment for a particular disease or condition in subjects identified is significantly different from treatment of all subjects without making such an identification (or without regard to the identification). Subjects needing or that could benefit from the treatment will receive it and subjects that do not need or would not benefit from the treatment will not receive it.

Accordingly, also disclosed herein are methods comprising taking particular actions following and based on the disclosed identifications. For example, disclosed are methods comprising creating a record of an identification (in physical—such as paper, electronic, or other—form, for example). Thus, for example, creating a record of an identification based on the disclosed methods differs physically and tangibly from merely performing a imaging, measurement, detection, comparison, analysis, assay, screen, etc. Such a record is particularly substantial and significant in that it allows the identification to be fixed in a tangible form that can be, for example, communicated to others (such as those who could treat, monitor, follow-up, advise, etc. the subject based on the identification); retained for later use or review; used as data to assess sets of subjects, treatment efficacy, accuracy of identifications based on different imagings, measurements, detections, comparisons, analyses, assays, screenings, etc., and the like. For example, such uses of records of identifications can be made, for example, by the same individual or entity as, by a different individual or entity than, or a combination of the same individual or entity as and a different individual or entity than, the individual or entity that made the record of the identification. The disclosed methods of creating a record can be combined with any one or more other methods disclosed herein, and in particular, with any one or more steps of the disclosed methods of identification.

As another example, disclosed are methods comprising making one or more further identifications based on one or more other identifications. For example, particular treatments, monitorings, follow-ups, advice, etc. can be identified based on the other identification. For example, identification of a subject as having a disease or condition with a high level of a particular component or characteristic can be further identified as a subject that could or should be treated with a therapy based on or directed to the high level component or characteristic. A record of such further identifications can be created (as described above, for example) and can be used in any suitable way. Such further identifications can be based, for example, directly on the other identifications, a record of such other identifications, or a combination. Such further identifications can be made, for example, by the same individual or entity as, by a different individual or entity than, or a combination of the same individual or entity as and a different individual or entity than, the individual or entity that made the other identifications. The disclosed methods of making a further identification can be combined with any one or more other methods disclosed herein, and in particular, with any one or more steps of the disclosed methods of identification.

As another example, disclosed are methods comprising treating, monitoring, following-up with, advising, etc. a subject identified in any of the disclosed methods. Also disclosed are methods comprising treating, monitoring, following-up with, advising, etc. a subject for which a record of an identification from any of the disclosed methods has been made. For example, particular treatments, monitorings, follow-ups, advice, etc. can be used based on an identification and/or based on a record of an identification. For example, a subject identified as having a disease or condition with a high level of a particular component or characteristic (and/or a subject for which a record has been made of such an identification) can be treated with a therapy based on or directed to the high level component or characteristic. Such treatments, monitorings, follow-ups, advice, etc. can be based, for example, directly on identifications, a record of such identifications, or a combination. Such treatments, monitorings, follow-ups, advice, etc. can be performed, for example, by the same individual or entity as, by a different individual or entity than, or a combination of the same individual or entity as and a different individual or entity than, the individual or entity that made the identifications and/or record of the identifications. The disclosed methods of treating, monitoring, following-up with, advising, etc. can be combined with any one or more other methods disclosed herein, and in particular, with any one or more steps of the disclosed methods of identification.

Methods of Treatment

Methods of treating or preventing diseases or disorders are provided using the disclosed compounds. The disclosed compounds can be used for targeting CD206 high expressing cells. The disclosed compounds can be used for targeting of macrophages for treatment of intracellular pathogens (*M. tuberculosis, F. tularensis, S. typhi*). The disclosed compounds can be used to target tumor-associated macrophages, e.g. to be used for treating cancer.

Macrophage-related and other CD206 high expressing cell-related diseases for which the compositions and methods herein may be used include, but are not limited to: acute disseminated encephalomyelitis (ADEM), Addison's disease, agammaglobulinemia, allergic diseases, alopecia areata, Alzheimer's disease, amyotrophic lateral sclerosis, ankylosing spondylitis, antiphospholipid syndrome, antisynthetase syndrome, arterial plaque disorder, asthma, atherosclerosis, atopic allergy, atopic dermatitis, autoimmune aplastic anemia, autoimmune cardiomyopathy, autoimmune enteropathy, autoimmune hemolytic anemia, autoimmune hepatitis, autoimmune hypothyroidism, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticarial, autoimmune uveitis, Balo disease/Balo concentric sclerosis, Behçet's disease, Berger's disease, Bickerstaffs encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, chronic venous stasis ulcers, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's Syndrome, cutaneous leukocytoclastic angiitis, Dego's disease, Dercum's disease, dermatitis herpetiformis, dermatomyositis, Diabetes mellitus type I, Diabetes mellitus type II diffuse cutaneous systemic sclerosis, Dressler's syndrome, drug-induced lupus, discoid lupus erythematosus, eczema, emphysema, endometriosis, enthesitis-related arthritis, eosinophilic fasciitis, eosinophilic gastroenteritis, eosinophilic pneumonia, epidermolysis bullosa acquisita, erythema nodosum, erythroblastosis fetalis, essential mixed cryoglobulinemia, Evan's syndrome, fibrodysplasia ossificans progressive, fibrosing alveolitis (or idiopathic pulmonary fibrosis), gastritis, gastrointestinal pemphigoid, Gaucher's disease, glomerulonephritis, Goodpasture's syndrome, Graves' disease, Guillain-Barré syndrome (GBS), Hashimoto's encephalopathy, Hashimoto's thyroiditis, heart disease, Henoch-Schonlein purpura, herpes gestationis (aka gestational pemphigoid), hidradenitis suppurativa, Hughes-Stovin syndrome, hypogammaglobulinemia, infectious diseases (including bacterial infectious diseases), idiopathic inflammatory demyelinating diseases, idiopathic pulmonary fibrosis, idiopathic thrombocytopenic purpura, IgA nephropathy, inclusion body myositis, inflammatory arthritis, inflammatory bowel disease, inflammatory dementia, interstitial cystitis, interstitial pneumonitis, juvenile idiopathic arthritis (aka juvenile rheumatoid arthritis), Kawasaki's disease, Lambert-Eaton myasthenic syndrome, leukocytoclastic vasculitis, lichen planus, lichen sclerosus, linear IgA disease (LAD), lupoid hepatitis (aka autoimmune hepatitis), lupus erythematosus, lymphomatoid granulomatosis, Majeed syndrome, malignancies including cancers (e.g., sarcoma, lymphoma, leukemia, carcinoma and melanoma), Ménière's disease, microscopic polyangiitis, Miller-Fisher syndrome, mixed connective tissue disease, morphea, Mucha-Habermann disease (aka *Pityriasis lichenoides* et *Varioliformis acuta*), multiple sclerosis, myasthenia gravis, myositis, narcolepsy, neuromyelitis optica (aka Devic's disease), neuromyotonia, occular cicatricial pemphigoid, opsoclonus myoclonus syndrome, Ord's thyroiditis, palindromic rheumatism, PANDAS (pediatric autoimmune neuropsychiatric disorders associated with *Streptococcus*), paraneoplastic cerebellar degeneration, Parkinsonian disorders, paroxysmal nocturnal hemoglobinuria (PNH), Parry Romberg syndrome, Parsonage-Turner syndrome, pars planitis, pemphigus vulgaris, peripheral artery disease, pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restenosis, restless leg syndrome, retroperitoneal fibrosis, rheumatoid arthritis, rheumatic fever, sarcoidosis, schizophrenia, Schmidt syndrome, Schnitzler syndrome, scleritis, scleroderma, sepsis, serum Sickness, Sjögren's syndrome, spondyloarthropathy, Still's disease (adult onset), stiff person syndrome, stroke, subacute bacterial endocarditis (SBE), Susac's syndrome, Sweet's syndrome, Sydenham chorea, sympathetic ophthalmia, systemic lupus erythematosus, Takayasu's arteritis, temporal arteritis (aka "giant cell arteritis"), thrombocytopenia, Tolosa-Hunt syndrome,) transplant (e.g., heart/lung transplants) rejection reactions, transverse myelitis, tuberculosis, ulcerative colitis, undifferentiated connective tissue disease, undifferentiated spondyloarthropathy, urticarial vasculitis, vasculitis, vitiligo, and Wegener's granulomatosis.

Tilmanocept as well as other related carrier molecules described in the '990 patent, as well as other carrier molecules based on a dextran backbone, bind to the mannose receptor protein CD206 found on the surface of macrophages and certain other cells (e.g., dendritic cells) when administered to mammals or when contacted with CD206 high expressing cells ex vivo. CD206 is a C-type lecithin binding protein found on the surface of macrophages and certain other types of cells. The finding that the CD206 protein, found for example on the surface of macrophages, is a gateway for tilmanocept binding in mammalian patients means that the tilmanocept carrier molecule (as well as related carrier molecules) can be used as the basis for preparing a variety of therapeutically and diagnostically effective molecular species for use in the diagnosis and/or treatment of macrophage related diseases and other diseases mediated by CD206 high expressing cells.

The disclosed compounds can include therapeutic agents including, but not limited to, cytotoxic agents, anti-angiogenic agents, pro-apoptotic agents, antibiotics, hormones, hormone antagonists, chemokines, drugs, prodrugs, toxins, enzymes, or other agents. The disclosed compounds can include chemotherapeutic agents; antibiotics; immunological adjuvants; compounds useful for treating tuberculosis; steroids; nucleotides; peptides; or proteins.

In certain embodiments, the compounds include an antimicrobial drug selected from the group comprising or consisting of: an antibiotic; an anti-tuberculosis antibiotic (such as isoniazid, ethambutol); an anti-retroviral drug, for example an inhibitor of reverse transcription (such as zidovudin) or a protease inhibitor (such as indinavir); drugs with effect on leishmaniasis (such as Meglumine antimoniate), or any combination thereof. In certain embodiments, the compounds include an anti-microbial active, such as amoxicillin, ampicillin, tetracyclines, aminoglycosides (e.g., streptomycin), macrolides (e.g., erythromycin and its relatives), chloramphenicol, ivermectin, rifamycins and polypeptide antibiotics (e.g., polymyxin, bacitracin) and zwittermicin. In certain embodiments, the compounds include an active selected from isoniazid, doxorubicin, streptomycin, and tetracycline, or any combination thereof. The disclosed compounds can be used, for example, to treat Tuberculosis, *Staphylococcus, Streptococcus*, yeast, *Serratia. E. coli*, and *Pseudomonas aeruginosa* infections.

In certain embodiments, the disclosed compounds advantageously have efficacy in the treatment of a condition or disorder caused by a micro-organism, for example, a condition or disorder selected from the group comprising or consisting of: tuberculosis and Leishmaniasis, or any combination thereof.

In certain embodiments, the disclosed compounds include a chemotherapeutic agent for the treatment or prevention of cancer. The cancer can be any cancer cell capable of metastasis. For example, the cancer can be a sarcoma, lymphoma, leukemia, carcinoma, blastoma, or germ cell tumor. A representative but non-limiting list of cancers that the disclosed compositions can be used to treat or prevent include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

In certain embodiments, the disclosed compounds are effective for treating autoimmune diseases, such as rheumatoid arthritis, lupus (SLE), or vasculitis. In certain embodiments, the disclosed compounds are effective for treating an inflammatory disease, such as Crohn's disease, inflammatory bowel disease, or collagen-vascular diseases.

One of ordinary skill in the art will appreciate that various kinds of molecules and compounds (e.g., therapeutic agents, detection labels, and combinations thereof) can be delivered to a cell or tissue using the disclosed compounds.

In one aspect, provided herein is a method of treating tuberculosis comprising administering to a subject in need thereof a compound as described herein wherein at least one A is a compound useful for treating tuberculosis.

In another aspect, provided herein is a method of diagnosing and treating a macrophage-mediated disorder comprising administering to a subject in need thereof an effective amount of a compound as described herein; and detecting the detection label at a predetermined location in the subject.

In another aspect, provided herein is a method of treating a macrophage-mediated disorder comprising administering to a subject in need thereof an effective amount of a compound as described herein.

In another aspect, provided herein is a method of treating a disease comprising administering to a subject in need thereof an effective amount of a compound according as described herein wherein the disease is an autoimmune disease, an inflammatory disease, or cancer.

In another aspect, provided herein is a method of targeting tumor-associated macrophages comprising administering to a subject in need thereof an effective amount of a compound as described herein.

In another aspect, provided herein is a method according to any of those described herein, wherein the compound contains at least one therapeutic agent and at least one detection label.

In another aspect, provided herein is a method according to any of those described herein, wherein a linker is used to attach the one or more CD206 targeting moieties, one or more therapeutic agents, and/or the one or more detection labels.

In another aspect, provided herein is a method according to any of those described herein wherein at least one $L_1$ comprises a degradable linker.

In another aspect, provided herein is a method according to any of those described herein, wherein at least one $L_1$ comprises a hydrolysable linker.

In another aspect, provided herein is a method according to any of those described herein, wherein at least one $L_1$ comprises an acid-sensitive linker.

In another aspect, provided herein is a method according to any of those described herein, wherein the macrophage-mediated disorder is selected from the group consisting of tuberculosis and Leishmaniasis.

In another aspect, provided herein is a method according to any of those described herein, wherein the disease is rheumatoid arthritis.

In another aspect, provided herein is a method according to any of those described herein, wherein the disorder is cancer.

In another aspect, provided herein is a method according to any of those described herein, wherein the cancer is a sarcoma, lymphoma, leukemia, carcinoma, blastoma, melanoma, or germ cell tumor.

In another aspect, provided herein is a method according to any of those described herein, wherein at least one A is a detection label and the detection label is a fluorophore.

In another aspect, provided herein is a method according to any of those described herein, wherein at least one $L_1$-A comprises a chelator.

Administration

The disclosed compounds can be administered via any suitable method. The disclosed compounds can be administered parenterally into the parenchyma or into the circulation so that the disclosed compounds reach target tissues (e.g., where cancer cells may be located). The disclosed compounds can be administered directly into or adjacent to a tumor mass. The disclosed compounds can be administered intravenously. In still other embodiments, the disclosed compounds can be administered intraperitoneally, intramuscularly, subcutaneously, intracavity, or transdermally.

Parenteral administration of the compounds, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

EXAMPLES

Example 1. Tilmanocept-Cy3 Binding to Human Macrophages

Figure 1B:
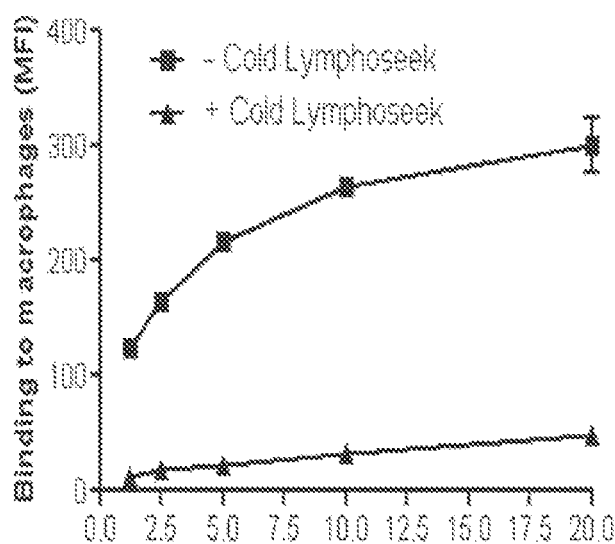

A quantity of PBMCs consisting of lymphocytes or macrophages was cultured for 5 days to enable blood monocytes to differentiate into macrophages (human monocyte-derived macrophages, or "MDMs"), and then pre-treated with or without unlabeled (cold) tilmanocept. Next, the cells were incubated with varying concentrations (1.25, 2.5, 5.0, 10 and 20 µg/mL) of Cy3-labeled tilmanocept (Cy3-tilmanocept). Tilmanocept binding to PBMC cell populations was analyzed by flow cytometry by gating separately for macrophages and lymphocytes. The resulting data showed that tilmanocept binds specifically to the macrophage population in a dose-dependent manner, as shown in FIG. 1A. FIG. 1A depicts fluorescence-activated cell sorting ("FACS") analysis of PBMCs, focusing on macrophages and lymphocytes. For the macrophages that were pre-treated with cold tilmanocept (100-fold excess), the binding of Cy3-tilmanocept was nearly abolished even at the highest concentrations, as shown in FIG. 1B (FACS analysis showing inhibition of Tilmanocept-Cy3 binding to macrophages in presence of unlabeled Tilmanocept **$P<0.005$).

Figure 1C:
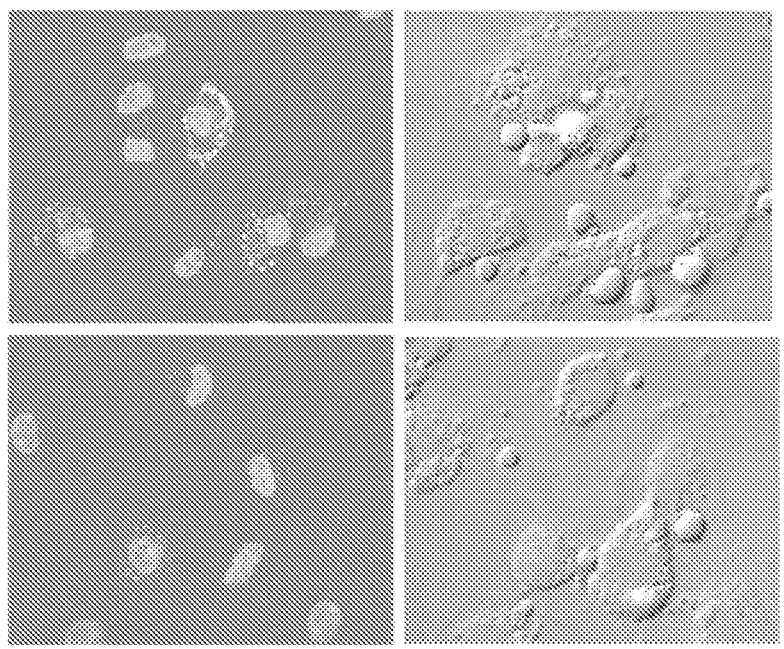
Figure 4:
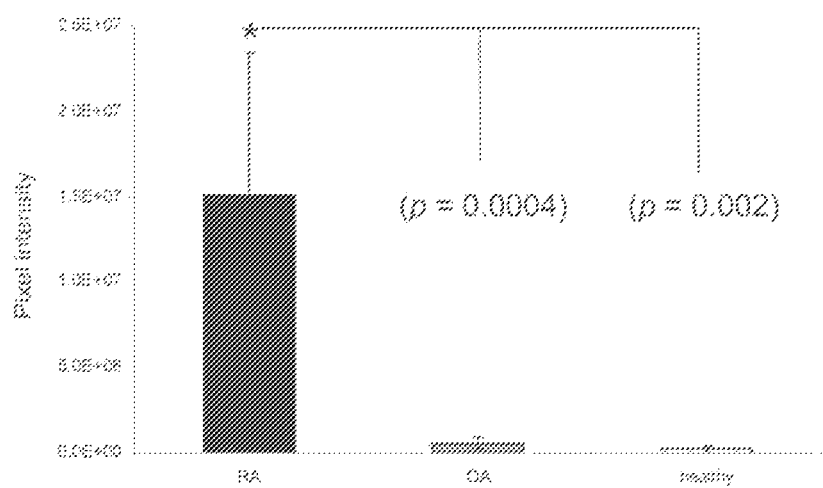
FIG. 4 shows the degree of macrophage invasion and CD206 residence in normal and OA tissue is significantly lower than in RA tissues.

To corroborate these findings, MDMs were treated in monolayer culture in a similar way, and fluorescence confocal microscopy experiments were performed. The binding of Cy3-tilmanocept to macrophages was readily apparent and this binding was nearly abolished for macrophages that were pre-treated with cold tilmanocept, as seen in FIG. 1C. Depicted data is representative of two independent experiments, each performed in duplicate, and the results were consistent with receptor-mediated binding of tilmanocept to macrophages. The upper and lower left images in FIG. 1C depict confocal microscopy representative images (magnification: 120×) which show binding (upper left) and inhibition of binding (lower left) of tilmanocept-Cy3 to macrophages in the absence or presence of tilmanocept with no fluorophore, respectively. The gray regions indicate macrophage nuclei, and the white portions indicate tilmanocept-Cy3. The upper and lower right images in FIG. 1C are DIC images which show the individual cell structure of the adjacent fluorescent images (to the left of each DIC image). "DIC" is Differential Interference Contrast (phase contrast microscopy).

Example 2. Co-Localization of Tilmanocept with the CD206 Mannose Receptor on Human Macrophages MDM monolayers were incubated with Cy3-tilmanocept for 10 minutes, fixed with paraformaldehyde, incubated with anti-MR primary Ab, and stained with Alexa Fluor 488-conjugated secondary Ab. The monolayers were then analyzed by confocal microscopy. FIG. 2 illustrates representative confocal images (magnification: 160×) showing expression of the CD206 MR (FIG. 2A), tilmanocept binding by the macrophage (FIG. 2B), and co-localization between the MR and tilmanocept in both confocal and phase contrast images (FIGS. 2C and 2D). The results shown are representative of three independent experiments.

Example 3. Binding of Tilmanocept to Macrophages Infected with Tuberculosis

Human monocyte-derived macrophages in monolayer culture that make up the components of the TB granulomas were infected with a GFP-expressing *M. tuberculosis* which was internalized by macrophages (GFP=green fluorescent protein). The infected cells were then exposed to tilmanocept which had been labeled with cyanine (Cy3) dye, and analyzed by confocal microscopy. Thus, FIG. 3 demonstrates that the Cy3-tilmanocept binds to, and is internalized by the macrophages.

Figure 5:
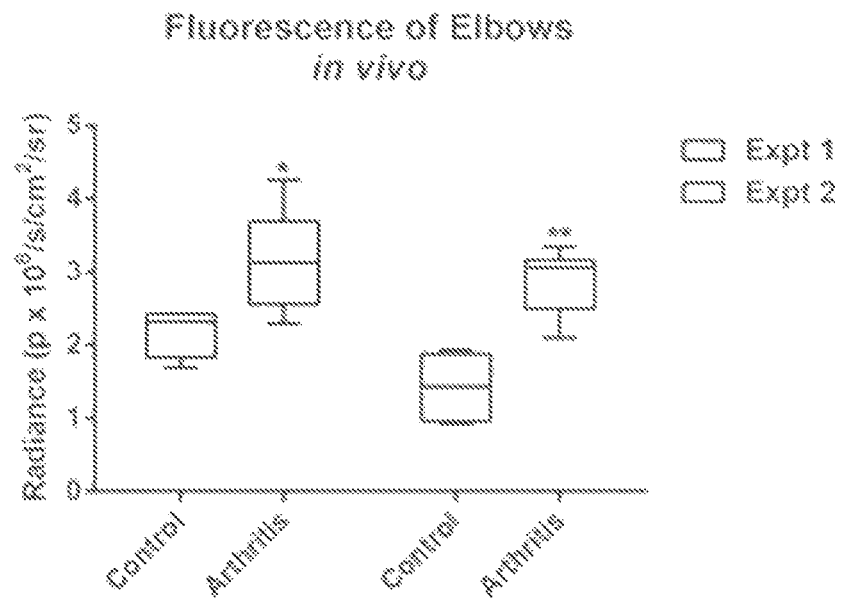
FIG. 5 shows specific fluorescence in arthritic knees and elbows.

Example 4. Localization of Tilmanocept in Synovial Fluid of Subjects with Rheumatoid Arthritis Tissues were probed with tilmanocept-Cy3, DAPI nuclear fluor, and anti CD206-cyanine green. The tissues and fluids were imaged by micro-fluorescence and compared to normal frozen archival tissue and synovial tissue procured from patients with osteoarthritis (OA). MP localization and degree of fluorescence were compared by digital image analysis. The results indicated that the synovial tissue and fluid from subjects with RA contain large macrophage populations that express high levels of CD206. Additionally, these MPs strongly localize Cy3-tilmanocept on CD206. In addition, the degree of macrophage invasion and CD206 residence in normal and OA tissue is significantly lower than in RA tissues, as seen in FIG. 5. Thus, the carrier molecules of the present invention, when provided with a detectable moiety such as a fluorophore, are able to not only diagnose RA from synovial fluid (either in vivo or ex vivo), but also can distinguish RA from OA.

Example 5. Imaging of Macrophages in Cartilage Antibody-Induced Arthritis in Mice Using Cy3-Tilmanocept Arthritis was induced in mice by injection of a five monoclonal antibody anti-cartilage cocktail followed in three days by an injection of *E. coli* lipopolysaccharide. The mice developed swollen and reddened joints in the feet, carpi, tarsi, elbows, and knees of variable degrees in 7-11 days, evidencing arthritis. Mice were imaged in vivo on days 7 or 8 and mice were euthanized on days 9 or 11. After euthanasia, the limbs were dissected, skin was removed, and the samples were reimaged (epifluorescent imaging), radiographed (Faxitron MX20) and then decalcified, embedded, and stained with H&E.

Figure 6:
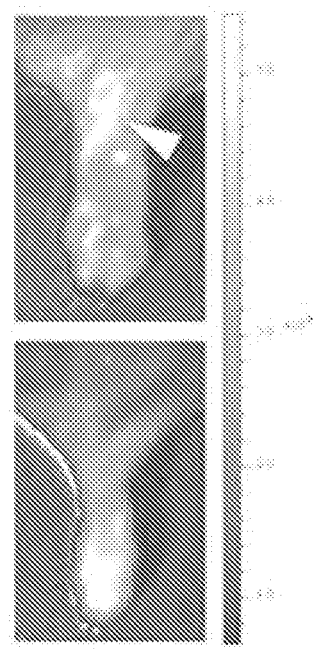
FIG. 6 shows in vivo fluorescence of the elbows and feet of a mouse with immune-mediated arthritis (top) and control mouse (bottom).
Figure 7:
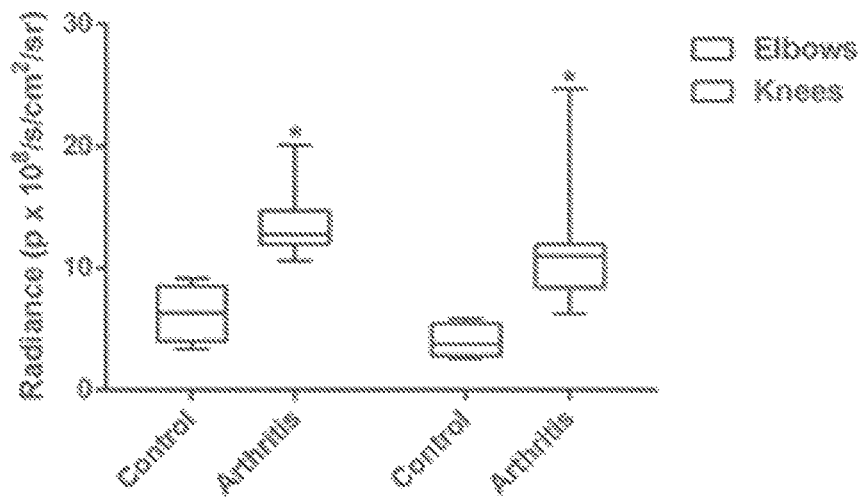
FIG. 7 shows ex vivo fluorescence data.
Figure 8:
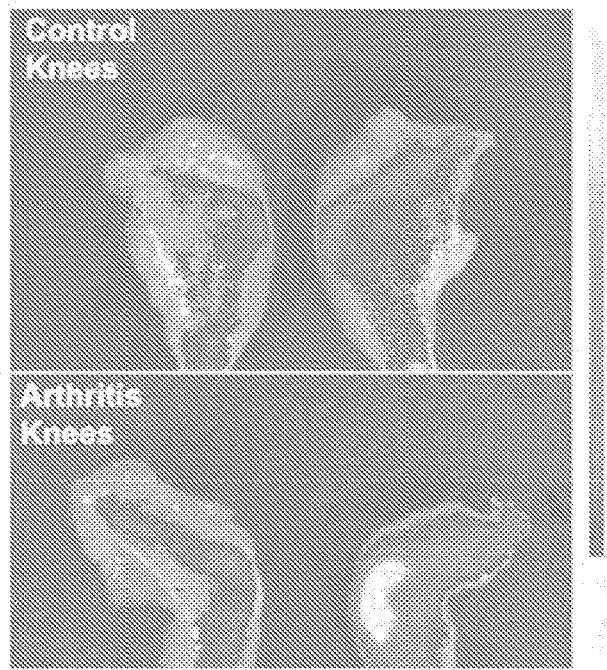
FIG. 8 shows ex vivo fluorescence of the knees of control mice and mice with immune-mediated arthritis
Figure 9:
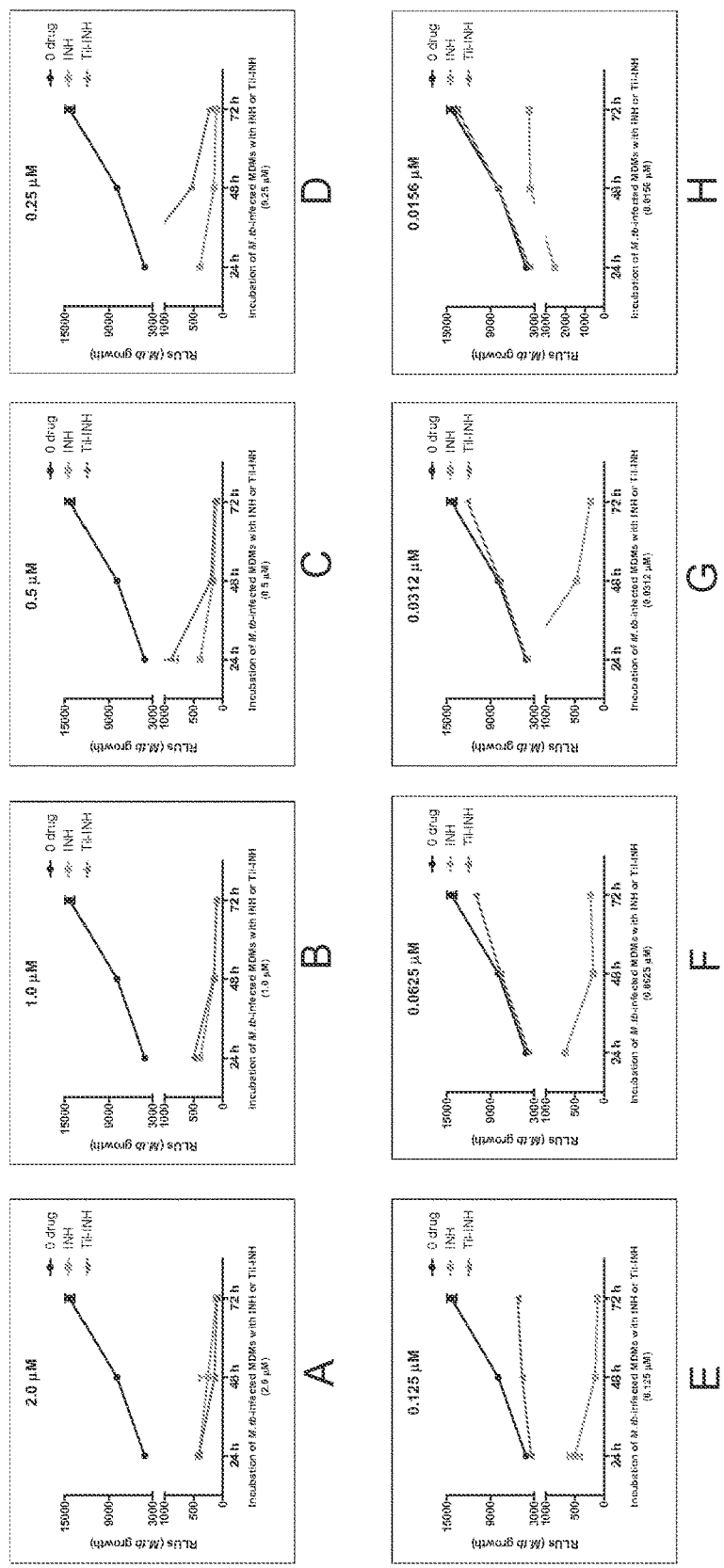
FIG. 9A-9G show that Til-INH was active inside macrophages.

For epifluorescent imaging, mice were injected intravenously with Cy3-tilmanocept, and epifluorescent imaging was conducted in vivo and ex vivo at 1-2 hours using an IVIS Lumina II machine (Caliper Life Sciences, Hopkinton, Mass.). Living Image software was used to visualize the visible and fluorescent images and to quantitate the number of photons using regions of interest ("ROI") and subtraction of background fluorescence. After euthanasia the limbs were dissected, skin was removed (except for the digits), and re-imaged. Specific fluorescence was detected in arthritic knees and elbows, as seen in FIG. 6. FIG. 7 depicts in vivo fluorescence of the elbows and feet of a mouse with immune-mediated arthritis (top) and control mouse (bottom). The mouse with arthritis had increased fluorescence due to Cy3-Tilmanocept in the elbow compared to the control mouse. There was background fluorescence from the skin, which was prominent on the feet. FIG. 8 shows ex vivo fluorescence data, and FIG. 9 depicts ex vivo fluorescence of the knees of control mice and mice with immune-mediated arthritis. Although both knees in the treated mouse (lower image) had arthritis, the knee on the right was affected more severely and had greater fluorescence due to Cy3-Tilmanocept labeling.

Example 6. Synthesis of Conjugated Tilmanocept-Linker

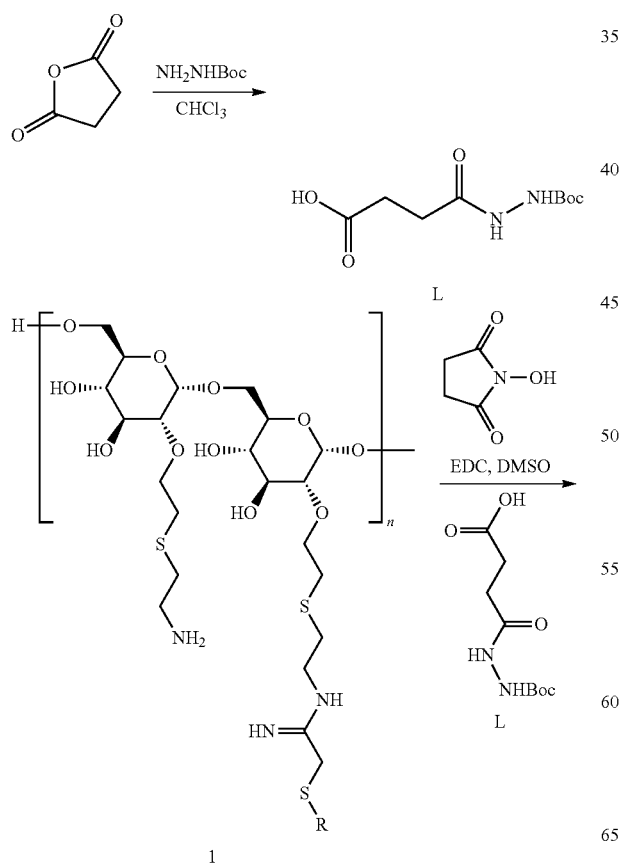

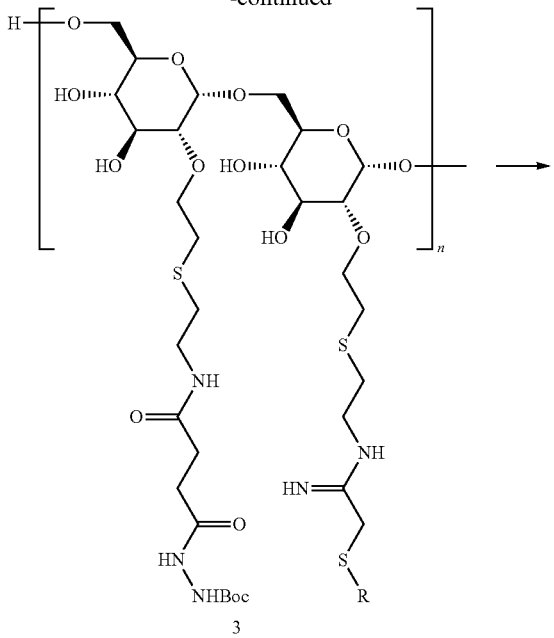

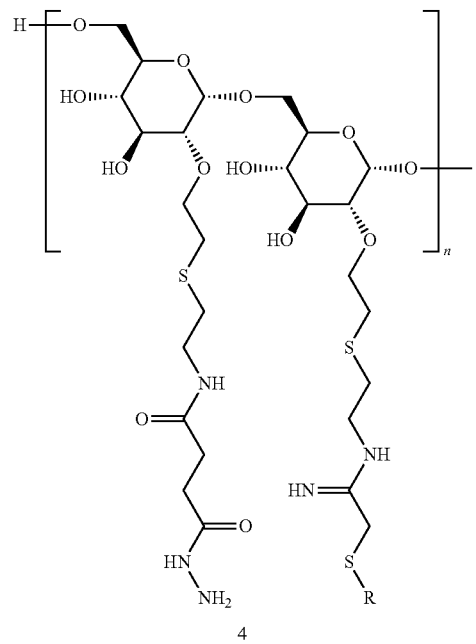

Synthesis of Linker L:

To a succinic anhydride (2 g, 20 mmol) solution in dichloromethane (80 mL), tert-butyl carbazate (2.6 g, 20 mmol) dissolved in dichloromethane (20 mL) was added over the period of 30 minutes. Then DMAP (0.020 g, 0.16 mmol) was added and the resulting reaction mixture was stirred under nitrogen overnight. Reaction mixture was concentrated under reduced pressure and the pure linker L was obtained after silica gel column chromatography (MeOH/CH$_2$Cl$_2$).

Conjugation of Linker to Tilmanocept:

To a solution of L (0.050 g, 0.21 mmol) in DMSO (3 mL) N-hydroxysuccinimide (0.052, 0.45 mmol) was added followed by Hunig's base (0.1 mL, 0.57 mmol) and then EDC (0.025 g, 0.13 mmol). The resulting reaction mixture was stirred for 48 h. After this time Tilmanocept (0.010 g) dissolved in 1 mL DMSO was added and the resulting reaction mixture was stirred for 24 h. Reaction mixture was quenched by slowly adding the reaction mixture into 20 mL deionized water. Modified polymer was purified from unconjugated small molecules by dialysis against deionized water. Pure polymer 3 was collected as pale yellow powder (13 mg) after overnight lyophilization.

Example 7. Conjugation of DOX to Modified Tilmanocept

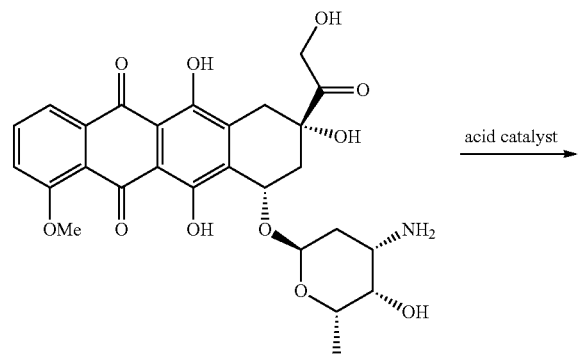

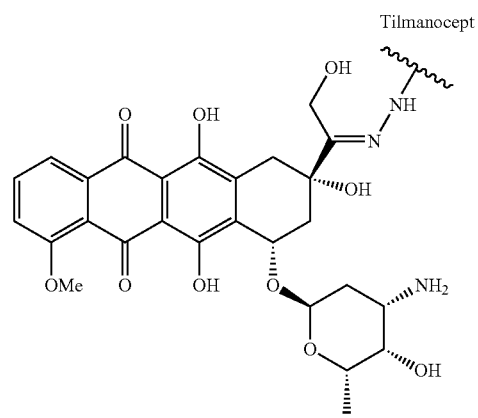

The linker conjugated polymer 3 was dissolved in DMSO (1 mL) followed by the addition of TFA (0.3 mL). The resulting reaction mixture was stirred for 3 hours to produce the intermediate 4. TFA was then removed under reduced pressure for a period of 2 hours and Dox.HCl (0.008 g) was added followed by TFA (10 µL). The resulting reaction mixture was stirred for 72 h and the residual TFA was then removed under reduced pressure for a period of 2 h. The reaction mixture was slowly added to 20 mL saturated $NaHCO_3$ solution. Dox conjugated polymer was purified from unconjugated Dox by using centricon filter of 3 kD cutoff.

Example 8. Conjugation of Isoniazid to Modified Tilmanocept

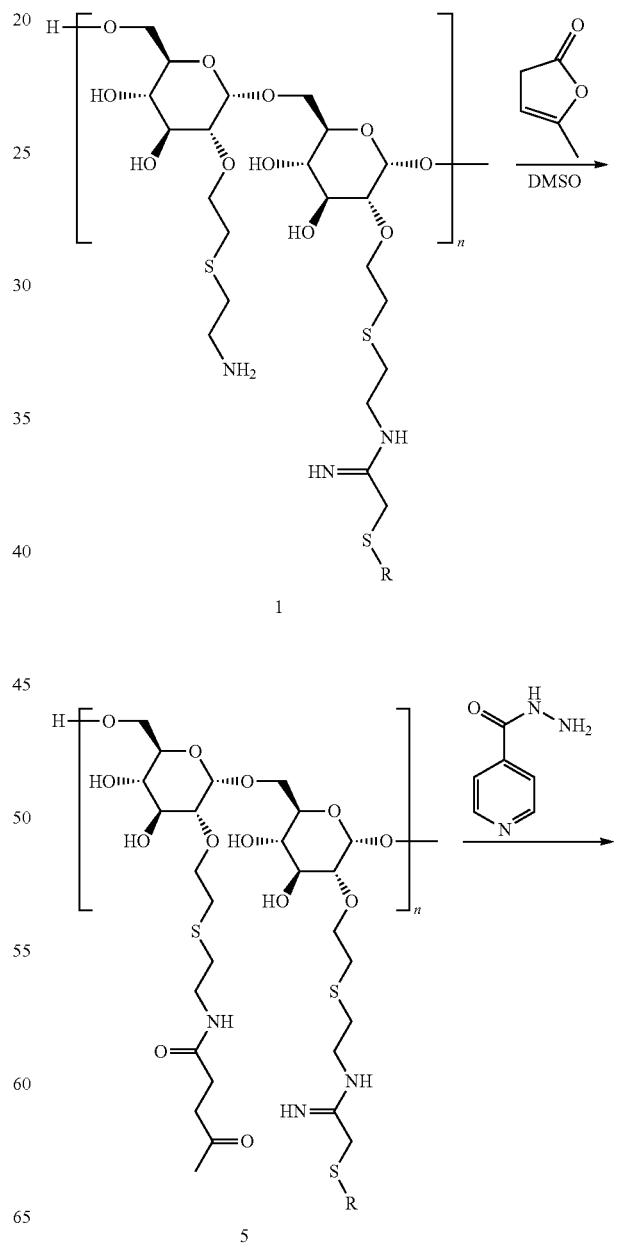

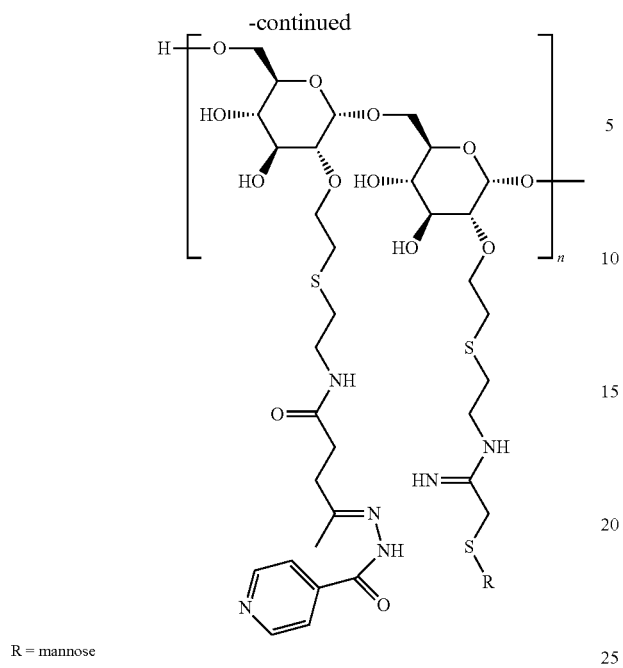

R = mannose

Tilmanocept (10 mg) was dissolved into anhydrous DMSO (2 mL), followed by the addition of angelica lactone (20 mg). The resulting reaction mixture was stirred under nitrogen for 3 hours. The unreacted angelica lactone was then removed under reduced pressure. The modified tilmanocept 5 thus obtained was again dissolved in 2 mL DMSO. To this solution isoniazid (10 mg) and trifluroacetic acid (30 µL) were added. The resulting reaction mixture was stirred at 37° C. for 48 hours. Reaction was then quenched by adding the reaction mixture to 20 mL saturated NaHCO$_3$ solution. The unreacted isoniazid was removed by centricon (3 KD cut off) filtration. Isoniazid conjugated tilmanocept was freeze dried and collected as a white powder.

Example 9. Anti-Bacterial Activity of Tilmanocept-Isoniazid Compared to Isoniazid Alone Against M.Tb in Human Macrophages 12 day-old human monocyte-derived macrophages (MDMs) were infected with a luciferase-expressing *M. tuberculosis* H37Rv strain (M.tb-Lux) at an MOI of 1:2 for 2 h to allow for bacterial uptake by MDMs. After washing off the extracellular bacteria, the infected monolayer was incubated with different concentrations of INH or Til-INH (2.0 µM through 0.0156 µM, drug equivalency) in low serum-containing media for up to 72 h. At different time points (24, 48, and 72 h), the monolayer was lysed and read for luminescence in RLUs which corresponds to the number of intracellular live bacilli.

Til-INH was active inside macrophages. (See FIG. 9). It was not found to be more potent than INH alone, which maintained its activity at as low as 0.0312 µM concentration against M.tb. However, Til-INH showed comparable anti-TB activity up to 0.5 µM concentration.

While the invention has been described in detail and with reference to specific embodiments thereof, it will be apparent to one skilled in the art that various changes and modifications can be made without departing from the spirit and scope of the invention.

What is claimed is:

1. A compound of Formula (II):

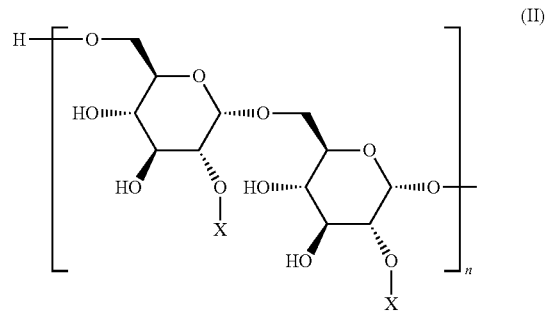

wherein each X is independently H, $L_1$-A, or $L_2$-R;

each $L_1$ and $L_2$ are independently linkers;

each A independently comprises one selected from the group consisting of a therapeutic agent, a detection label, and H;

each R independently comprises one selected from the group consisting of a CD206 targeting moiety and H; and n is an integer greater than zero; and wherein at least one X is $L_1$-A wherein $L_1$ comprises a hydrazone and at least one X is $L_2$-R wherein at least one $L_2$ comprises —(CH$_2$)pS(CH$_2$)qNH—, wherein p and q independently are integers from 0 to 5.

2. A compound according to claim 1, wherein at least one R is selected from mannose, fucose, and n-acetylglucosamine.

3. A compound according to claim 1, wherein at least one A is selected from a chemotherapeutic agent; an antibiotic; an immunological adjuvant; a compounds useful for treating tuberculosis; a steroid; a nucleotide; a peptide; a protein; microRNA; siRNA; an antiviral; an antigens; or a metal.

4. A compound according to claim 1, wherein at least one A is a compound useful for treating tuberculosis.

5. A compound according to claim 1, wherein at least one A is doxorubicin, isoniazid, gadolinium, gallium, silver, or a silver antibiotic.

6. A compound according to claim 1 wherein at least one $L_1$ is a $C_{2-12}$ hydrocarbon chain optionally interrupted by up to three heteroatoms selected from the group consisting of O, S and N.

7. A compound according to claim 1 wherein at least one $L_1$ comprises (CH$_2$)$_p$S(CH$_2$)$_q$NH, wherein p and q are integers from 0 to 5.

8. A compound according to claim 1 wherein at least one $L_2$ is a $C_{2-12}$ hydrocarbon chain optionally interrupted by up to three heteroatoms selected from the group consisting of O, S and N.

9. A compound according to claim 1, wherein at least one $L_1$-A comprises a chelator.

10. A compound of Formula (4):
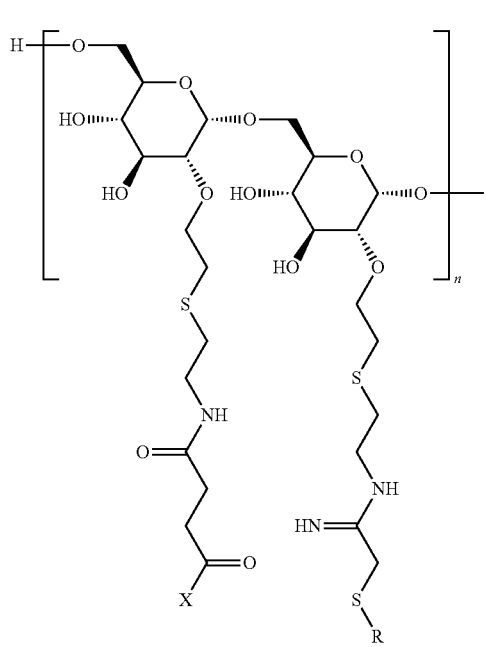
(4)
wherein
R is mannose,
n is an integer greater than zero, and
X is
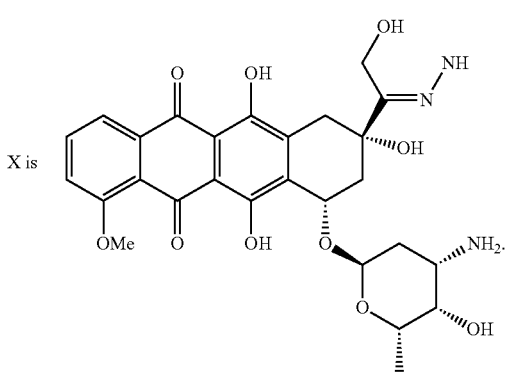 [SMILES: COc1cccc2c1C(=O)c1c(O)c3c(c(O)c1C2=O)C[C@@](O)(/C(CO)=N/N)C[C@@H]3O[C@H]1C[C@H](N)[C@H](O)[C@H](C)O1]
11. A compound of Formula (7):
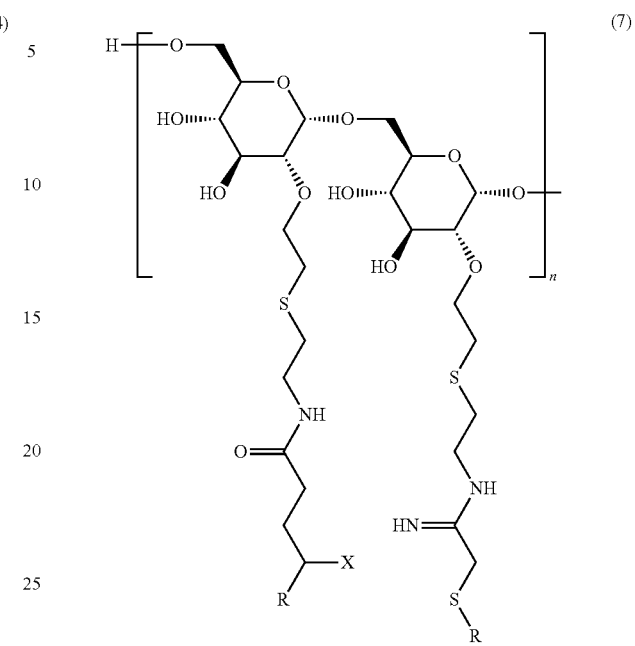
(7)
wherein
R is mannose,
R' is H or $CH_3$,
n is an integer greater than zero, and
X is
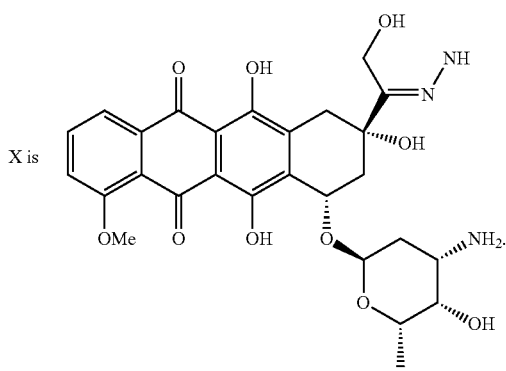 [SMILES: COc1cccc2c1C(=O)c1c(O)c3c(c(O)c1C2=O)C[C@@](O)(/C(CO)=N/N)C[C@@H]3O[C@H]1C[C@H](N)[C@H](O)[C@H](C)O1]
* * * * *

UNITED STATES PATENT AND TRADEMARK OFFICE
CERTIFICATE OF CORRECTION

PATENT NO. : 10,806,803 B2
APPLICATION NO. : 15/326985
DATED : October 20, 2020
INVENTOR(S) : Larry Schlesinger et al.

It is certified that error appears in the above-identified patent and that said Letters Patent is hereby corrected as shown below:

On the Title Page

Item (71) Applicants read:
(71) Applicants: OHIO STATE INNOVATION FOUNDATION, Columbus, OH (US); CARDINAL HEALTH 414, LLC, Dublin, OH (US); Frederick O. Cope, Dublin, OH (US)

Should read:
(71) Applicants: OHIO STATE INNOVATION FOUNDATION, Columbus, OH (US); CARDINAL HEALTH 414, LLC, Dublin, OH (US)

Signed and Sealed this
Seventh Day of March, 2023

Katherine Kelly Vidal
*Director of the United States Patent and Trademark Office*